United States Patent [19]

Rieke

[11] Patent Number: 5,358,546
[45] Date of Patent: Oct. 25, 1994

[54] HIGHLY REACTIVE FORMS OF ZINC AND REAGENTS THEREOF

[75] Inventor: Reuben D. Rieke, Lincoln, Nebr.

[73] Assignee: Board of Regents of the University of Nebraska, Lincoln, Nebr.

[21] Appl. No.: 830,629

[22] Filed: Feb. 4, 1992

[51] Int. Cl.⁵ .................... B22F 1/00; C21B 11/10; C07F 3/00
[52] U.S. Cl. ........................ 75/252; 75/371; 75/721; 75/10.62; 556/118; 252/512
[58] Field of Search ............... 556/118; 75/10.62, 252, 75/371, 721

[56] References Cited

U.S. PATENT DOCUMENTS

| | | | |
|---|---|---|---|
| 3,100,782 | 8/1963 | Joly et al. | 260/345.2 |
| 3,660,443 | 5/1972 | Boissieras et al. | 260/429.7 |
| 3,755,395 | 8/1973 | Bakassian et al. | 260/429.9 |
| 4,087,468 | 5/1978 | Solomon | 568/807 |
| 4,107,180 | 8/1978 | Dye et al. | 260/338 |

FOREIGN PATENT DOCUMENTS

252766 1/1988 European Pat. Off. .
61-019707A2 1/1986 Japan .

OTHER PUBLICATIONS

R. D. McCullough et al., *J. Chem. Soc., Chem. Commun.*, 70–73 (1992).
R. D. Rieke, Abstract of National Institute of Health Grant No. GM35153 (1992).
R. T. Arnold et al., "Activated Metals. A Procedure for the Preparation of Activated Magnesium and Zinc", *Synthetic Communications*, 7, 223–232 (1977).
E. Bouhlel et al., "A Convenient Procedure for the Preparation of Reactive Zinc for the Reformatsky Reaction", *Synthetic Communications*, 21, 133–136 (1991).
J. L. Dye, "Macrocylic chemistry in reducing environments: From concentrated metal solutions to crystalline electrides", *Pure & Appl. Chem.*, 61, 1555–1562 (1989).
R. M. Wehmeyer, "The Preparation and Chemistry of Active Copper, Nickel, and Zinc", Ph.D. Thesis, The University of Nebraska-Lincoln, Dec. 1988.
L.-S. Zhu, "The Preparation of Novel Organozinc Reagents Using Highly Reactive Zinc", Ph.D. Thesis, The University of Nebraska-Lincoln, Dec. 1991.
R. F. Abdulla, *Aldrichimica Acta*, 21, 31 (1988).
N. E. Alami et al., *J. Organomet. Chem.*, 348, 1 (1988).
M. Bellassoued et al., *J. Organomet. Chem.*, 280, 165 (1985).
E. R. Burkhardt et al., *J. Org. Chem.*, 50, 416 (1985).
D. J. Burton et al., *J. Org. Chem.*, 54, 613 (1989).
E. Erdik, *Tetrahedron*, 43, 2203 (1987).
J. K. Gawronski, *Tetrahedron Letters*, 25, 2605 (1984).
J. Grondin et al., *J. Organomet. Chem.*, 362, 237 (1989).
J. J. Habeeb et al., *J. Organomet. Chem.*, 185, 117 (1980).
B. H. Han et al., *J. Org. Chem.*, 47, 5030 (1982).
B. H. Han et al., *J. of the Korean Chemical Society*, 29, 557 (1985).
S. M. Hannick et al., *J. Org. Chem.*, 48, 3833 (1983).
S. W. Hansen et al., *J. Fluorine Chem.*, 35, 415 (1987).
P. L. Heinze et al., *J. Fluorine Chem.*, 31, 115 (1986).
M. Isobe et al., *Chem. Lett.*, 679 (1977).
R. A. Kjonaas et al., *J. Org. Chem.*, 51, 3993 (1986).
K. J. Klabunde et al., *J. Org. Chem.*, 44, 3901 (1979).
P. Knochel et al., *J. Org. Chem.*, 53, 2390 (1988).
P. Kovacic et al., *J. Polym. Sci., Polym. Chem. Ed.*, 17, 1963 (1979).

(List continued on next page.)

*Primary Examiner*—José G. Dees
*Assistant Examiner*—Porfirio Nazario
*Attorney, Agent, or Firm*—Merchant, Gould, Smith, Edell, Welter & Schmidt

[57] ABSTRACT

A novel zerovalent zinc species and an organozinc reagent are disclosed. The zerovalent zinc species is directly produced by reaction of a reducing agent on a zinc salt, preferably $Zn(CN)_2$. The organozinc reagent results from the reaction of the zerovalent zinc species and an organic compound having one or more stable anionic leaving groups. These organozinc reagents include a wide spectrum of functional groups in the organic radical, and are useful in a variety of reactions schemes.

23 Claims, No Drawings

OTHER PUBLICATIONS

B. E. Lenk, M. S. Thesis, University of Nebraska, Lincoln, Nebraska, 1988.
B. H. Lipshutz et al., *Tetrahedron,* 42, 2873 (1986).
R. M. Magid, *Tetrahedron,* 36, 1901 (1980).
T. O. Murdock et al., *J. Org. Chem.,* 41, 1076 (1976).
E. Nakamura et al., *J. Am. Chem. Soc.,* 109, 8056 (1987).
E. Negishi et al., *J. Org. Chem.,* 42, 1821 (1977).
E. Negishi, *Organometallics in Organic Synthesis,* New York: Wiley (1980).
E. Negishi et al., *Tetrahedron Lett.,* 24, 5181 (1983).
M. S. Newman et al., *J. Amer. Chem. Soc.,* 77, 946 (1955).
H. Ochiai et al., *J. Org. Chem.,* 52, 4418 (1987).
C. Petrier et al., *Tetrahedron Letters,* 27, 3149 (1986).
G. Picotin et al., *J. Org. Chem.,* 52, 4796 (1987).
M. W. Rathke, *Org. React.,* 22, 423 (1975).
R. D. Rieke et al., *J. Chem. Soc., Chem. Commun.,* 269 (1973).
R. D. Rieke et al., *J. Org. Chem.,* 38, 1430 (1973).
R. D. Rieke, *Use of Activated Metals in Organic and Organometallic Synthesis,* Springer-Verlag: New York (1975), pp. 1–31.
R. D. Rieke et al., *Synthesis,* 452 (1975).
R. D. Rieke, *Accounts of Chem. Res.,* 10, 301 (1977).
R. D. Rieke, *J. Org. Chem.,* 46, 4323 (1981).
R. D. Rieke et al., *High Energy Processes in Organometallic Chemistry,* ACS Symposium Series No. 333, ACS 1987, Ch. 14, 223.
R. D. Rieke, *Science,* 246, 1260 (1989).
R. D. Rieke et al., *Synth. Commun.,* 19, 1833 (1989).
R. D. Rieke et al., *Synth. Commun.,* 20, 2711 (1990).
F. G. Saitkulova et al., *Zh. Org. Khim.,* 12, 969 (1976) (Abstract only).
F. G. Saitkulova et al., *Izv. Vyssh. Uchebn. Zaved., Khim. Khim. Tekhnol.,* 20, 669 (1977) (Abstract only).
K. Sekiya et al., *Tetrahedron Letters,* 29, 5155 (1988).
R. L. Shriner, *Org. React.,* 1, 1 (1942).
R. D. Smith et al., *Organic Syntheses,* Wiley: New York, (1973); Collect. vol. V, p. 855.
R. M. Souto et al., *Macromolecules,* 23, 1268 (1990).
D. E. Stack et al., *J. Am. Chem. Soc.,* 113, 4672 (1991).
V. Y. Tamaru et al., *Angew. Chem.,* 99, 1193 (1987).
W. ten Hoeve et al., *J. Am. Chem. Soc.,* 113, 5887 (1991).
J. M. Tour et al., *J. Am. Chem. Soc.,* 113, 2309 (1991).
M. Ueda et al., *Macromolecules,* 24, 2694 (1991).
S. J. Uhm, "Preparation of activated zinc metal and its reactions with organic halides in presence of various Lewis bases", Thesis, University of North Carolina, Chapel Hill, N.C. (1974).
R. A. Watson et al., *Tetrahedron Letters,* 27, 1437 (1986).
Y. Wei et al., *Chem. Mater.,* 3, 888 (1991).
H. Xiong et al., *Tetrahedron Letters,* 39, 5269 (1991).
T. Yamamoto et al., *Makromol. Chem., Rapid Commun.,* 6, 671 (1985).
T. Yamamoto et al., *Makromol. Chem.,* 190, 1649 (1989).
T. Yamamoto et al., *Polym. J.,* 22, 187 (1990).
M. C. P. Yeh et al., *Tetrahedron Letters,* 29, 2395 (1988).
M. C. P. Yeh et al., *Tetrahedron Letters,* 29, 6693 (1988).
L. Zhu et al., *J. Org. Chem.,* 56, 1445 (1991).
L. Zhu et al., *Tetrahedron Letters,* 32, 2864 (1991).

HIGHLY REACTIVE FORMS OF ZINC AND REAGENTS THEREOF

The present invention was made with Government support under Contract No. GM35153 awarded by the National Institute of Health. The Government has certain rights in the invention.

BACKGROUND OF THE INVENTION

Organozinc reagents are highly desirable reagents for organic synthesis. They possess many attributes that are distinct from other organometallic reagents. For example, they often react stereoselectively and regioselectively and do not possess the extreme nucleophilicity of such reagents as Grignard reagents. Consequently, organozinc reagents can generate distinctly different chemistry from that of other organometallic reagents, such as the synthesis of organic compounds that are highly functionalized.

Although there are several procedures known for the reduction of metal salts to metal powders reactive towards oxidative addition, each metal typically requires unique permutations of the procedures to obtain a reactive species. There is no standardized approach that can produce metal powders of identical, or even similar reactivity. For example, magnesium metal in the form of a black powder can be obtained by reducing magnesium salts in an ethereal solvent with molten sodium or potassium. However, the use of an alkaline metal in conjunction with an electron carrier such as naphthalene can produce magnesium powder of different reactivity.

Organozinc compounds are typically prepared by the oxidative addition of zinc metal to alkyl iodides. The reaction is limited, however, due to the low reactivity of the metal. Several methods have been used to activate zinc towards oxidative addition reactions. These include methods such as washing with HCl solution, using a Zn-Cu couple, ultrasound irradiation, and metal-solvent cocondensation, for example. In spite of these methods, the direct oxidative addition of zinc metal to organic halides has been limited to relatively reactive halides such as alkyl iodides or $\alpha$-haloesters. Recently, zinc homoenolates of alkyl propionates were prepared by ring-opening reactions of 1-siloxy-1-alkoxycyclopropanes. However, most alkyl bromides, alkyl chlorides, vinyl halides, and aryl halides do not directly react with zinc metal.

Because of the low reactivity of metallic zinc, very little has been done to study the reactivity of organozinc halides (RZnX) or $R_2Zn$. The conjugate addition of alkyl halides to $\alpha,\beta$-unsaturated ketones mediated by a Zn/Cu couple in aqueous media has been reported. Furthermore, copper (I) salts have been used to mediate the 1,4-addition of organozinc species to $\alpha,\beta$-unsaturated ketones. Lithium and magnesium triorganozincates also undergo 1,4-additions with $\alpha,\beta$-unsaturated ketones. However, only one of the three organic moieties is transferred in the process. This problem has been solved to some degree by utilizing only one equivalent of the alkyllithium and two equivalents of methyllithium in forming these reagents. The methyl group appears to be a good, nontransferable "dummy" ligand for the lithium trialkylzincates. However, since trialkylzincate reagents are derived from the Grignard or lithium precursors, they offer no distinct advantage over the known zinc cuprate reagents, which do not have wide applicability.

The synthesis of many drugs, agrochemicals, monomers for use in polymers, highly conducting polymers, dyes, synthetics fibers, fluorocarbons, and a long list of other specialty chemicals require the use of organometallic intermediates at some stage of the synthesis. An important organometallic intermediate in various of these syntheses is an organozinc compound. Many of these organozinc compounds can only be prepared via a transmetallation reaction using Grignard reagents (organomagnesium reagents) or organolithium reagents. One of the major problems with these methods, however, is that the presence of many desirable functional groups (i.e., esters, ketones, nitriles, epoxides, $\alpha,\beta$-unsaturated ketones, etc.) in the organic portion of the compounds is precluded.

Therefore, a highly reactive zinc that would directly oxidatively add to a wide variety of carbon-halogen bonds in the presence of many or all of the above mentioned functional groups is needed. The present invention fulfills a need for such a highly reactive zinc reagent and resultant organozinc reagents having a variety of functional groups. These organozinc reagents can be utilized in further synthesis of various chemical compounds that can be useful in drugs, agrochemicals, monomers for polymers, highly conducting polymers, etc.

An object of the invention is to produce a zinc species that is more reactive than those obtained from traditional methods. Another object of the invention is to produce a zinc species that is highly reactive towards oxidative addition. Yet another object of the invention is the direct production of a wide variety of organozinc compounds, e.g., aryl, heterocyclic, arylalkyl, and polymeric zinc reagents that can undergo a number of valuable synthetic reactions. Still another object of the invention is to produce a wide variety of organozinc reagents that contain a broad spectrum of functional groups such as esters, ketones, nitrites, halides, amides, carbamates, epoxides, aldehydes, $\alpha,\beta$-unsaturated enones (e.g., esters and ketones), sulfoxides, sulfones, etc. Furthermore, an object of the invention is the synthesis of new organic compounds or the synthesis of known organic compounds using more effective and/or more direct synthetic methods.

SUMMARY OF THE INVENTION

These and other objects are achieved by the present invention which is directed to the use of a highly reactive zinc species to form new organozinc reagents and synthetic reactions performed with these organozinc reagents. As used herein, the phrase "highly reactive" refers to the reactivity of the zinc species in organic reactions, particularly oxidative addition reactions. A zinc species is highly reactive if it reacts with a wide variety of primary, secondary, and tertiary alkyl, vinyl, and aryl halides in relatively high yields, for example, in greater than about 30% yields, preferably in greater than about 50% yields, and more preferably in greater than about 70% yields.

The highly reactive zinc species of the present invention is composed of formally zerovalent zinc metal atoms in a finely divided powdered form. Preferably, the zerovalent highly reactive zinc species is a mixture or combination of zerovalent zinc metal atoms and an alkali metal salt. More preferably, the zerovalent zinc metal atoms are in combination with an alkali metal salt of a cyanide, halide, or both, and most preferably, in combination with an alkali metal salt of a cyanide or both a cyanide and a halide.

The zerovalent highly reactive zinc species of the present invention is prepared from the reduction of a zinc(II) salt, the counterion of which can be any of a variety of anions that does not contain an acidic proton. For example, the anion can be a sulfate, nitrate, nitrite, acetate, cyanide, or halide. Preferably, the anion is a halide or cyanide, more preferably the anion is iodine, chlorine, bromine, and cyanide, and most preferably cyanide.

In the present invention, highly reactive zinc, readily undergoes oxidative addition to organic compounds, preferably highly functionalized organic compounds, under mild conditions to generate corresponding organozinc reagents in excellent yields. An organozinc reagent of the present invention includes a mixture or combination of an organic mono- or poly- zinc compound and an alkali metal salt of a cyanide, halide, or both, wherein the organic radical of the zinc compound is an aliphatic, aryl, heterocyclic, arylalkyl, or polymeric group. Preferably, the organic radical of the zinc compound is an aliphatic, aryl, heterocyclic, or arylalkyl group. Also, preferably, the organozinc reagent of the present invention includes a mixture or combination of an organic mono- or poly- zinc compound and an alkali metal salt of a cyanide.

In the context of the present invention, the term "aliphatic" means a saturated or unsaturated linear, branched, or cyclic hydrocarbon radical. This term is used to encompass alkyl and vinyl radicals, for example. The term "alkyl" means a saturated linear, branched, or cyclic hydrocarbon radical. The term "heterocyclic" means a mono- or polynuclear cyclic radical containing carbons and one or more heteroatoms such as nitrogen, oxygen, phosphorus, silicon, or sulfur or a combination thereof in the ring or rings, including but not limited to pyridine, pyrrol, indole, thiazole, pyrazine, guanine, cytosine, thyamine, adenine, uredine, uracil, oxazole, pyrazole, hydantoin, piperazine, quinoline, xanthene, 1,10-phenanthroline, thiophene, and acridine. The term "aryl" means a mono- or polynuclear aromatic hydrocarbon radical. The term "arylalkyl" means a linear, branched, or cyclic alkyl hydrocarbon radical having a mono- or polynuclear aromatic hydrocarbon or heterocyclic substituent. The term "polymeric" or "polymer" is used herein in its most general sense to mean a compound of repeating structural units.

The present invention is also directed to the preparation of an organozinc reagent. This method of preparation involves contacting an organic compound having one or more stable anionic leaving groups with a first combination of zerovalent zinc metal atoms and an alkali metal salt to produce a second combination of an organic mono- or poly- zinc compound and the alkali metal salt. Preferably the alkali metal salt is a salt of a halide or cyanide, or both. More preferably, it is a salt of a cyanide or both a cyanide and halide. The organic radical of the organic compound having one or more stable anionic leaving groups is an aliphatic, aryl, heterocyclic, arylalkyl, or polymeric group.

The organozinc reagents of the present invention display surprising and unexpected reactivity and usefulness. For example, when mediated by Cu(I) salts, they can crosscouple with acid chlorides, conjugatively add to $\alpha,\beta$-unsaturated ketones, and regioselectively undergo $S_N2'$ substitution reactions with allylic halides. When mediated by Pd(0) catalysts, they can cross-couple with aryl or vinyl halides. They can also undergo a variety of intramolecular and polymerization reactions. The yields of these reactions are typically very high and reproducible. Accordingly, this approach considerably increases the synthetic potential of organozinc intermediates.

DETAILED DESCRIPTION OF THE INVENTION

Organozinc reagents are finding ever increasing use in organic synthesis. This stems not only from their unique chemical reactivity but also from their stability and ease of manipulation. Except for a relatively small range of highly reactive organic halides, the direct formation of organozinc reagents from zinc metal and organic halides, acetates, etc., was not previously possible. However, the present highly reactive zinc will undergo oxidative addition to a wide variety of organic compounds, e.g., alkyl, vinyl, and aryl iodides, bromides, and chlorides, to generate the corresponding organozinc reagent. Significantly, most of these reactions can be carried out at room temperature or slightly above. The resulting organozinc reagents are very stable. Of special note is the toleration of the reaction toward the presence of functional groups, and often particularly unexpected functional groups. As a result, highly functionalized organozinc reagents can be prepared by the present invention. This allows the synthesis of many molecules to be shortened considerably and made viable commercial candidates. The highly reactive zinc can also be used to carry out other name reactions on substrates that now are not possible using the standard forms of zinc. Also, a number of intramolecular reactions can now be carried out.

The present invention is based upon the discovery that a highly reactive zinc metal species displays surprising and unexpected reactivity and usefulness in organic synthetic procedures. For example, the highly reactive zinc species displays reactivity toward a wide variety of highly functionalized aliphatic, aryl, heterocyclic, arylalkyl, and polymeric compounds to form organozinc reagents.

The Zinc Species and Methods of Preparation

The highly reactive zinc species of the present invention is composed of formally zerovalent zinc metal atoms in a finely divided powdered form. The formally zerovalent zinc metal atoms are in combination with an alkali metal salt. By "formally zerovalent" it is meant that the formal oxidation state, or charge, is equal to the group number (i.e., 2) minus the number of unshared electrons (i.e., 2) minus the number of bonds (i.e., 0). Preferably, the zerovalent highly reactive zinc species is a mixture or combination of zerovalent zinc metal atoms and an alkali metal salt. Preferably, the alkali metal salt is a salt of the counterion associated with the Zn(II) salt. More preferably, the zerovalent highly reactive zinc species includes an alkali metal salt of a cyanide, halide, or both, and most preferably alkali metal salts of a cyanide or a cyanide and a halide. The mixture or combination is highly dispersible in ethereal, polyethereal, or hydrocarbon solvents.

Although not intending to be a limitation of the invention, it is believed that the zinc species is a cluster of zinc atoms associated in some manner with the alkali metal salts provided by the salt produced from the cation of the reducing agent and the anion of the zinc salt starting material and/or the coordinate complexing agent for the zinc salt starting material, if present. The cluster-salt association is most likely a surface phenomenon and is believed to facilitate the oxidative transfer reaction between the zinc species and the organic compounds in the formation of the organozinc reagents.

The zerovalent highly reactive zinc species of the present invention is prepared from the reduction of a zinc(II) salt, the counterion of which can be any of a variety of anions that does not contain an acidic proton. For example, the anion can be a sulfate, nitrate, nitrite, acetate, cyanide, or halide. Preferably, the anion is a halide or cyanide. More preferably, the anion of the Zn(II) salt is CN, Br, Cl or I, at least because they yield a zinc powder of higher reactivity relative to the other anions. Most preferably, the anion of the Zn(II) salt is CN, at least because it yields a zinc powder of significantly high reactivity relative to the other anions. Thus, useful species that can be reduced to form the highly reactive zerovalent zinc species of the present invention include, but are not limited to, $ZnCl_2$, $ZnBr_2$, $ZnI_2$, $Zn(CN)_2$, $ZnSO_4$, $Zn(NO_3)_2$, $Zn(CH_3CO_2)_2$, $ZnF_2$, and $Zn(NO_2)_2$. The preferred zinc salts are $ZnCl_2$, $ZnBr_2$, $ZnI_2$, $ZnF_2$, and $Zn(CN)_2$. The more preferred zinc salts are $ZnCl_2$, $ZnBr_2$, $ZnI_2$, and $Zn(CN)_2$, with $Zn(CN)_2$ being the most preferred.

The commercially available zinc halide N,N,N'N'-tetramethylethylenediamine complexes (e.g., $ZnCl_2$-TMEDA) can be used as a relatively nonhygroscopic substitute for the zinc halide chosen in many instances. This type of TMEDA complex is also either available commercially or can be prepared for the other zinc halides and zinc cyanide. Reduction of this complex gives highly reactive zinc with similar reactivity to the highly reactive zinc prepared from anhydrous zinc halides. This is a desirable starting material in some situations at least because it is not air sensitive.

In addition to $Zn(CN)_2$, which is generally insoluble in most ethereal, polyethereal, and hydrocarbon solvents, soluble forms of $Zn(CN)_2$ can be used in the method of the present invention. Such soluble forms include a coordinate complexing agent, such as an alkali metal halide salt in coordination with the $Zn(CN)_2$. Preferably, the coordinate complexing agent is an alkali metal halide salt, more preferably it is a lithium halide salt, and most preferably it is lithium bromide or chloride.

Generally, the reducing agent can be any reducing agent that is capable of reducing Zn(II) salts. Typically, this means that the reducing agent has a reduction potential of about −1.0 volts or more negative relative to the standard calomel electrode (SCE). It is preferred, however, that the reducing agent has a reduction potential of about −1.5 volts or more negative, and most preferred that the reducing agent has a reduction potential of about −2.0 volts or more negative, relative to SCE. Examples of useable reducing agents include: alkali and alkaline earth metals; alkali and alkaline earth metal salts of aromatic anions (i.e., aromatic electron transfer compounds), such as sodium or lithium naphthalenide; metal hydrides, such as sodium borohydride, sodium hydride; metal intercalated graphites; and alkali metals dissolved in glymes or ethers.

Preferably the reducing agent is an alkali metal reducing agent, such as an alkali metal, an alkali metal dissolved in glymes or ethers, or an alkali metal salt of an electron transfer compound. More preferably, the reducing agent is an alkali metal salt of an electron transfer compound, i.e., a combination of an alkali metal cation and an anion of an electron transfer compound, referred to herein as an "alkali metal complex." The electron transfer compound preferably has a reduction potential of −0.5 volts, versus the standard calomel electrode (SCE), or more negative. More preferably, the electron transfer compound is an aromatic electron transfer compound.

Examples of useful "alkali metal complex" reducing agents include, but are not limited to, complexes of an alkali metal and an aromatic electron transfer compound; alkali metal-polyether solvates; alkali metal-crown ether solvates; alkali metal-cryptate solvates, etc. Preferably, the alkali metal complex reducing agent is sodium, potassium, lithium, or cesium naphthalenide, anthracenide, biphenylide, or benzophenone. More preferably, the reducing agent is a complex of an alkali metal cation and naphthalene. Most preferably, the reducing agent is a complex of lithium and naphthalene.

The process of reduction of the various Zn(II) salts to produce the zerovalent highly reactive zinc species of the present invention is conducted under conditions designed to prevent its reoxidation. Generally, these conditions include use of a nonhydroxylic solvent, and the exclusion of oxygen. Also, the conditions are controlled so as to promote the existence of the zinc atoms in a finely divided powder because large clusters of zinc atoms generally means lower reactivity.

Preferably, these conditions include temperatures of about 100° C. or less, an inert atmosphere, e.g., an argon or nitrogen atmosphere, and a reaction time of about ten hours or less. More preferably, the temperature is about 80° C. or less and the reaction time is about five hours or less. Most preferably, the reactions are conducted at temperatures of about 20° C. to about 30° C., and the reaction time is about two hours or less.

As stated above, the solvent is a nonhydroxylic solvent. Preferably, it is an ethereal, polyethereal, or hydrocarbon solvent. Examples of such solvents include ethyl ether, methyl-t-butyl ether, tetrahydrofuran (THF), 1,2-dimethoxyethane (DME or glyme), diglyme, triglyme, benzene, xylene, hexanes, and the like. More preferably, the reaction is carried out in an ethereal or polyethereal solvent, and most preferably in tetrahydrofuran. If a hydrocarbon solvent (e.g., benzene, xylene, hexanes, etc.) is used, it preferably contains a secondary solubilizing agent such as N,N,N',N'-tetramethylethylenediamine (TMEDA) to assist in solubilizing the starting materials. If the reducing agent is an alkali metal reducing agent, but not an alkali metal salt of an electron transfer compound, the solvent is one whose boiling point exceeds the melting point of the alkali metal.

There are several methods of preparation of the zerovalent highly reactive zinc species of the present invention. For example, the Zn(II) salt can be prepared by the combination of an equivalent amount of an alkali metal, such as K or Na, in a solvent whose boiling point exceeds the melting point of the alkali metal, such as THF or glyme. By this, it is meant that about two moles, i.e., about 1.8–2.2 moles, of an alkali metal are used per mole of zinc salt.

Another method for the preparation of a reactive zinc species involves a one-step reduction of a Zn(II) salt. This method is referred to herein as "Method A" and is represented by the reduction of $ZnCl_2$ and $Zn(CN)_2$ in Example 1. Specifically, this method includes the reduction of a Zn(II) salt in the presence of an alkali metal, such as lithium, and an effective catalytic amount of an electron transfer compound, such as the aromatic electron transfer compound naphthalene. With respect to this method, by an "effective catalytic amount" it is meant that a sufficient amount of the electron transfer compound is present to effect the reduction in less than about 24 hours, preferably in less than about 10 hours. The electron transfer compound is typically present in no greater than about 10 mole-%, preferably no greater than about 6 mole-%, and most preferably between about 2 mole-% and about 5 mole-%, of the alkali metal present. The alkali metal is present in an equivalent amount, i.e., in a range of about 1.8–2.2 moles per mole of zinc salt being reduced. It is desirable, however, to use a slight excess of the zinc salt relative to the alkali metal, to decrease the chance that the reducing agent could interfere with the subsequent use of the highly reactive zinc.

The reduction is typically complete in about ten hours, and preferably in about five hours, with vigorous stirring of the mixture. For certain embodiments, the reaction is observed to be "complete" when the green color, which is evidence of an alkali metal/aromatic electron transfer complex, disappears. This occurs, for example, with the when the relatively insoluble $Zn(CN)_2$ when Method A is used. For other embodiments, the reaction is observed to be "complete" when the green color appears, and remains. For example, this would occur if a soluble zinc salt, such as $ZnCl_2$, were used in Method A with an excess of the alkali metal and electron carrier, relative to the zinc salt. For still other embodiments, completion of the reduction reaction is evidenced by the disappearance of lithium and/or lack of formation of the bright green lithium naphthalenide anion. With the zinc halides, vigorous stirring is generally necessary to prevent the resultant reduced zinc from coating the unused alkali metal and stopping the reaction. With the zinc cyanides, this coating problem is not generally observed, although stirring is desirable.

In this one-step preparation method with generally soluble zinc salts, such as $ZnCl_2$ in THF, the solubilized Zn(II) salt, is generally always in excess in the reaction flask, relative to the amount of the alkali metal/electron transfer complex present. Herein, "solubilized" salt means the portion of the Zn(II) salt that has gone into solution. With generally insoluble zinc salts, such as $Zn(CN)_2$ in THF, the formation of the alkali metal/electron transfer complex is faster than the dissolution of the zinc salt. Thus, the alkali metal complex is generally always in excess in the reaction flask, relative to the amount of the solubilized Zn(II) salt. Although this has been observed for these particular species, this is not meant to be a limitation of the invention. For the soluble zinc salts, this is not necessarily the most preferred method of reduction because the surface of the lithium metal can be coated with zinc, which slows down the reduction. For the insoluble zinc salts, however, this is the most preferred method of reduction because it yields a very reactive zinc using a one step procedure.

A third method for the preparation of a reactive zinc species involves a two-step reduction of a Zn(II) salt using a preformed reducing agent. This method is referred to herein as "Method B" and is represented by the reduction of $ZnCl_2$ and $Zn(CN)_2$ in Example 1. By "preformed" it is meant that for each mole of the alkali metal, about 1–1.2 moles of an electron transfer compound are allowed to react substantially completely, i.e., until substantially all the alkali metal is consumed, before contacting any zinc salts. The formation of the preformed reducing agent preferably takes place in an ethereal, polyetheral, or hydrocarbon solvent, and generally is substantially complete in less than about eight hours, preferably in less than about two hours.

An approximate equivalent amount of the zinc salt in a solvent, e.g., $ZnCl_2$ in THF, is then slowly (over a period of about 5 to 15 minutes) transferred into the solution of the preformed reducing agent, e.g., lithium naphthalenide in THF. Alternatively, the preformed reducing agent can be added to the zinc salt. Preferably, the procedure is carried out in this latter way if the zinc salt is relatively insoluble in the solvent chosen. Whichever the direction of transfer, it is preferably done at a rate to ensure that the preformed reducing agent is in excess relative to the solubilized zinc. For the more soluble zinc halides, the transfer of the preformed reducing agent to the zinc salt is done more slowly (over a period of about 15 to 120 minutes) than the transfer of the preformed reducing agent to the zinc salt. In this way, the reactivity of the resultant zerovalent zinc powder is not decreased, which is believed to result from unreduced zinc ions being adsorbed on the zinc metal surface.

The reduction of the Zn(II) salt in the second step of this two step method using a preformed reducing agent is typically carried out in less than about eight hours, preferably in less than about two hours, and more preferably in less than about one hour. Preferably, the total reaction time for both steps is less than about eight hours. This two-step method is advantageous for soluble Zn(II) salts, when compared to Method A, at least because it involves a shorter reaction time and it decreases, if not eliminates, the problem of the resultant reduced zinc coating the alkali metal.

Generally this method forms highly reactive zinc of approximately the same reactivity as does Method A, whether the Zn(II) salt is soluble or not. That is, although the zinc powder formed from zinc cyanides is more highly reactive than the zinc powder formed from zinc halides, the zinc powder formed from zinc halides is of approximately the same reactivity whether formed by Method A or Method B. Similarly, the zinc powder formed from zinc cyanides is of approximately the same reactivity whether formed by Method A or Method B. This is evidenced by the fact that zinc powder formed from the same Zn(II) salt, whether prepared by Method A or Method B, reacts at substantially the same rate with a wide range of organic halides, and produces similar yields.

A fourth method for the preparation of a reactive zinc species involves a two-step reduction of a Zn(II) salt in the presence of an excess of an alkali metal. This method is referred to herein as "Method C" and is represented by the reduction of $ZnCl_2$ in Example 1. The reducing agent is formed from an alkali metal and an effective catalytic amount of an electron transfer compound. By an "effective catalytic amount" it is meant that a sufficient amount of the electron transfer compound is present to effect the reduction in less than about three hours, preferably in less than about two hours. Preferably, this involves the use of no greater than about 10 mole-% of the electron transfer reagent, more preferably no greater than about 6 mole-%, and most preferably between about 2 and about 5 mole-%, of the alkali metal present. The alkali metal is present in an equivalent amount, i.e., in a range of about 1.8–2.2 moles per mole of zinc salt being reduced. Thus, a solution of the resultant alkali metal complex reducing agent, i.e., the complex of the alkali metal and electron transfer compound, contains unreacted alkali metal.

A zinc salt, preferably a zinc salt solution, e.g., $ZnCl_2$ in THF, or a zinc salt suspension, e.g., $Zn(CN)_2$ in THF, is then slowly transferred into the solution of the alkali metal reducing agent, e.g., lithium naphthalenide in THF, containing unreacted alkali metal, e.g., lithium. By "slowly" it is meant that the Zn(II) salt is added to the solution of the reducing agent containing unreacted alkali metal at a rate that ensures the presence of excess alkali metal complex reducing agent relative to solubilized Zn(II) salt. This is evidenced by adding the Zn(II) salt at a rate such that the color of the reducing agent solution remains dark green, if a complex of an alkali metal and aromatic electron transfer compound is used. Although not intending to be a limitation to the invention in any way, it is believed that as the reducing agent is consumed, the recovered naphthalene reacts with the unreacted lithium to form lithium naphthalenide until all the lithium is consumed. This is unexpected because the small amount of electron carrier is expected to lead to long reduction times of several hours and even days, rather than minutes. In contrast, the relatively short reduction times with small amount of electron carrier makes this an especially appealing method.

Method C is the most preferred of the three methods specifically described, especially for the relatively soluble Zn(II) salts, such as zinc halides in ethereal solvents, at least because a more reactive and uniform zerovalent zinc species is produced. This is evidenced by the fact that the zerovalent highly reactive zinc species produced using this method typically provides more reproducible yields of highly functionalized organic compounds in subsequent reactions than does the zinc species produced from the same Zn(II) salt using either Method A or Method B. Furthermore, as compared to either of Methods A or B, this method greatly shortens the reduction time. For example, the highly reactive zinc can be formed in less than about three hours, preferably in less than about two hours, more preferably in less than about one hour, and most preferably in less than about 30 minutes, from the time the soluble Zn(II) salt is initially added to the alkali metal complex reducing agent. Also, as compared to Method B in which a preformed reducing agent is used, this method reduces the amount of electron transfer agent required. Thus, this method is especially useful for large scale reactions. In some situations, however, such as when a relatively insoluble Zn(II) salt like $Zn(CN)_2$, is used, Method A may be preferred, even if the reaction times are longer, at least because everything can be carried out in a single flask, i.e., no transfers are necessary, and the amount of electron transfer compound required is small.

The physical appearance of the zerovalent highly reactive zinc formed from any of the methods described herein typically depends on the rate of stirring and/or the rate of transfer. For example, with respect to Method A, the appearance of the zinc depends on the rate of stirring, and with respect to Methods B and C, the appearance of the zinc depends on the speed of the addition of the zinc salt or the reducing agent, in addition to the rate of stirring. A slow addition of about three seconds per drop results in an extremely fine black slurry of active zinc. The slurry takes several hours to settle and can easily be transferred by a cannula. With faster addition, about one second or less per drop, the active zinc formed is sponge shaped. Although it is believed that either of these physical forms of the zinc does not detrimentally effect its reactivity, if the zinc is not in a finely divided form, i.e., if it is sintered into large shiny pieces, it will not be very reactive.

The alkali metal complex reducing agents, e.g., lithium naphthalenide, can also be generated by electrochemical reduction of an electron transfer compound, e.g., naphthalene, using an alkali metal salt, e.g., a lithium halide, as the electrolyte. That is, an alkali metal complex reducing agent can be formed electrochemically. This can be carried out in an electrochemical cell containing an ethereal or polyethereal solvent using an electrode of palladium, platinum, carbon, or gold. Useful electrodes can be in any of a variety of forms. They can be solid, porous, or in the form of a slurry. The electrochemical route is advantageous and preferred at least because it avoids the use of alkali metals, which can be quite dangerous.

As a representative example of this procedure, naphthalene can be reduced in an inert atmosphere in the presence of a lithium salt, as the electrolyte, in THF. The electrode can be a large surface area electrode to facilitate the reduction. Once the lithium naphthalenide is formed, it can be transferred to the zinc salt, or the zinc salt can be transferred to it, for formation of the zerovalent highly reactive zinc.

Whichever method is chosen, the zerovalent highly reactive zinc is typically in the form of a finely divided black powder. Once formed it can be isolated and washed to remove any unreacted starting materials, side products, or excess reducing agent, if so desired. It is generally stable and can be stored for several years at temperatures ranging from 0° C. to 30° C. It can be stored in a dry state, in mineral oil as a paste, in an ethereal or hydrocarbon solvent as a suspension, or in a paraffin wax matrix. It is desirable, however, for the zerovalent highly reactive zinc to be stored under an inert atmosphere of argon or nitrogen.

The Organozinc Reagents

The zerovalent highly reactive zinc species of the present invention readily undergoes oxidative addition to a wide variety of organic compounds to form organozinc reagents. Significantly, the reaction will tolerate a wide spectrum of functional groups on the organic compounds. These organozinc reagents can be used to create unique organic species, such as highly functionalized biphenyl compounds, highly functionalized benzene derivatives, symmetrical and unsymmetrical substituted 1,3-butadienes, highly functionalized ketones, esters, amides, nitriles, or halides, or known organic compounds from unique synthetic routes.

Generally, the organozinc reagent of the present invention includes an aliphatic, aryl, heterocyclic, arylalkyl, or polymeric mono- or poly- zinc compound. Preferably, the organozinc reagent is a mixture or combination of an aliphatic, aryl, heterocyclic, arylalkyl, polymeric mono- or poly- zinc compound and an alkali metal salt. More preferably, the organozinc reagent contains an alkali metal salt of a cyanide, halide, or both and most preferably of a cyanide or a cyanide and a halide. The zinc moiety and alkali metal salts are derived from the foregoing zerovalent zinc species. Although not intending to be a limitation of the invention, it is believed that the zinc moiety or moieties of the organic zinc compound associate in some manner with the alkali metal salts present to form the organozinc reagent. It is further believed that this association is in part responsible for the novel and selective reactivity of the organozinc reagent of this invention.

The molecular size of the organozinc reagents can range from monomeric organic compounds, typically having from 1 to about 300 carbons, to polymeric compounds having molecular weights up to and including the million range. The organic radical of the organozinc compound can be an aliphatic, aryl, arylalkyl, heterocyclic, or polymeric group. That is, the organic radical can be saturated, unsaturated, cyclic, aromatic, or heterocyclic containing nitrogen, oxygen, sulfur, phosphorus, silicon, or combinations thereof in the heteronucleus. Preferably, the organic radical of the organozinc compound is an aliphatic, aryl, heterocyclic, or arylalkyl group, and more preferably an arylalkyl or heterocyclic group. Most preferably, the organic radical of the organozinc compound is a heterocyclic group. Of the possible heterocycles, a sulfur-containing heterocycle is preferred.

Preferred aliphatic, aryl, heterocyclic, and arylalkyl groups include linear or branched alkyl, cycloalkyl, allyl, vinyl, phenyl, benzyl, pyridyl, quinolinyl, piperadinyl, cytosinyl, uracinyl, quaninyl, adenosinyl, pyrrolyl, thiazolyl, thiophene, and phenyl alkyl groups, as well as the hydrocarbon substituted and/or functionalized forms thereof. The hydrocarbon substituents can be one or more of such groups as alkyl, cycloalkyl, heterocyclic, olefinic, and aromatic groups as well as combinations thereof, each substituent preferably having from 1 to about 30 carbon atoms.

The aliphatic, aryl, arylalkyl, heterocyclic, or polymeric group of the organozinc reagent may optionally, and preferably, be functionalized with such groups as amides, nitriles, esters, ketones, allyls, ethers, carbamates, acetyls, imines, enones, epoxides, olefins, aldehydes, sulfoxides, sulfones, other halides, or any combination of these groups. Preferably, these functional groups are esters, nitriles, ketones, amides, halides, acetyls, enones, epoxides, olefins, ethers, or any combination of these groups.

The organozinc reagents are produced by the reaction of the highly reactive zinc species of the present invention with an organic compound having at least one stable anionic leaving group. That is, the method for preparation of an organozinc reagent of the present invention includes contacting an organic compound having one or more stable anionic leaving groups with a first combination of zerovalent zinc metal atoms and an alkali metal salt, preferably a salt of cyanide, to produce a second combination of an organic mono- or poly- zinc compound and the alkali metal salt.

The organic compound having at least one stable anionic leaving group, i.e., the starting material, preferably includes an organic radical selected from an aliphatic, aryl, heterocyclic, arylalkyl, and polymeric radical, more preferably, an aliphatic, aryl, heterocyclic, and arylalkyl group, and most preferably, a heterocyclic group, such as sulfur, oxygen, nitrogen, etc., as discussed above. The organic radical can optionally, and preferably, be functionalized with amides, nitriles, esters, ketones, allyls, ethers, carbamates, acetyls, imines, enones, epoxides, olefins, aldehydes, sulfoxides, sulfones, other halides, or any combination of these groups. More preferably, these functional groups are esters, nitriles, ketones, amides, halides, acetyls, enones, epoxides, olefins, ethers, or any combination of these groups.

The stable anionic leaving group of the organic compound starting material can be a halide, tosylate, triflate, phenolate, brosylate, trialkyl amine, triaryl amine, mixed tri(alkyl/aryl)amine, trialkyl phosphine, triaryl phosphine, mixed tri(alkyl/aryl)phosphine, trialkyl stannane, triaryl stannane, mixed tri(alkyl/aryl)stannane, thiophene ($-SC_6H_5$), phenolate ($-OC_6H_5$), and the like. By "mixed tri(alkyl/aryl)" amine, phosphine, stannane, it is meant that the nitrogen, phosphorus, and tin can be substituted with both alkyl and aryl groups. For example, the anionic leaving group can be $P(CH_3)_2(C_6H_5)$. Preferably, the anionic leaving group is a halide or triflate, and more preferably, a halide. That is, more preferably the organozinc reagents include organozinc halides, i.e., aliphatic, aryl, heterocyclic, arylalkyl, or polymeric compounds having one or more halide groups. Thus, organozinc halides are understood to include vinyl halides. Most preferably, the halide groups are iodide, chloride, and bromide. If the halide group is a chloride, in certain reactions an alkali metal iodide can be added to the reaction mixture to improve the reactivity.

Typical yields of the organozinc reagents are greater than about 30%, preferably greater than about 50%, and more preferably greater than about 70%. In some instances the organozinc reagents can be produced in nearly quantitative yields. Unless otherwise indicated, percentages herein refer to mole percentages, and are typically based on the amount of the starting organic compound having at least one stable anionic leaving group.

Although the highly reactive zinc used in the formation of the organozinc reagents of the present invention can be that prepared by any of the methods described herein, it is preferably prepared as described in Method C, particularly if zinc halides are used. This is because the zinc prepared in this manner produces more reproducible results. Also, it is easier, less costly, and requires less time to prepare. Furthermore, it is easier to purify than the zinc produced in Methods A and B. If zinc cyanides are used, however, typically Method A is preferred, at least because it is easier, less costly, and more efficient.

Examples of organic halides that react with the highly reactive zinc species of the present invention include, but are not limited to, 1-bromooctane, 1-bromo-6-cyanohexane, 1-bromo-6-chlorohexane, 1-chlorooctane, 1-bromo-3-phenoxypropane, 1-bromo-5-phenoxypentane, bromocyclohexane, 1-bromoadamantane, m-bromotoluene, m-bromoanisol, p-chlorotoluene, 1-bromopropane, 1-iodobutane, o-cyanophenyl bromide, allyl chloride, ethyl 4-bromobenzoate, 1,4-dibromobenzene, 2,5-dibromothiophene, etc. See the Tables below for specific examples of organozinc compounds prepared by the method of the present invention.

The reactions are generally conducted under conditions designed to preserve the integrity of the organozinc reagents. These conditions include, for example, the exclusion of water and oxygen. Typically, the reactions are carried out in the same medium used to produce the highly reactive zinc species. Preferably, the reactions are carried out in an ethereal, polyethereal, or hydrocarbon solvent. More preferably, the reactions are carried out in an ethereal or polyethereal solvent. Most preferably the reactions are carried out in THF.

The reactions of organic compounds with a stable leaving group, e.g., organic halides, with the zerovalent highly reactive zinc species of the present invention are typically carried out at temperatures between about −110° C. and about 250° C., preferably between about −30° C. and about 150° C. More preferably, the reactions are carried out at temperatures less than about 100° C. Most preferably, the reactions are carried out at temperatures between about 20° C. and about 100° C. As a general matter, the reactions of aryl halides require higher temperatures than the reactions with alkyl halides. The reactions are typically complete within about six hours, and preferably within about two hours.

The highly reactive zinc species and the reactive organic compound, e.g., organic halide, with which it reacts, are preferably present in an amount such that the ratio of zinc to reactive organic compound is about 0.9–4 moles of zinc to 1 mole of reactive organic compound. More preferably, the ratio is 0.9–1.1 moles zinc to 1 mole reactive compound, i.e., about an equimolar amount. Most preferably, the zinc is present in an excess amount, i.e., at least about 1.1 moles zinc to 1.0 mole reactive organic compound.

Although the organozinc reagents contain functional groups such as allyls, ethers, esters, nitriles, amides, ketones, etc., they are generally stable at ambient temperatures. That is, they do not typically self-react, or otherwise decompose, to a significant extent. To prevent any significant amount of decomposition, the organozinc reagents of the present invention are preferably stored within a temperature range of about −100° C. to about 200° C., under argon or nitrogen.

REACTIVITY OF THE ORGANOZINC REAGENTS

In general, the organozinc reagents undergo coupling reactions with organic electrophiles, i.e., compounds that are deficient in electrons, such as carboxylic acid halides, aldehydes, $\alpha,\beta$-unsaturated carbonyl compounds, epoxides, and the like. A typical method for preparation of a functionalized organic compound from the organozinc reagents of the present invention includes combining an organozinc reagent and an organic electrophile to produce a coupling of the organic radical of the organozinc reagent and the organic group of the organic electrophile, wherein the organozinc reagent is a combination of an aliphatic, aryl, heterocyclic, arylalkyl or polymeric mono- or poly- zinc compound and an alkali metal salt, preferably a salt of a cyanide. One of the carbons of the electrophilic group and the carbanion of the organozinc reagent, i.e., the carbon to which the zinc is attached, are the sites for coupling. Although the organic electrophile starting material can contain any type of electrophilic group, such as carboxylic acid halides, aldehydes, enones, imines, epoxides, $\alpha,\beta$-unsaturated aldehydes, ketones, esters, and amides, and the like, it preferably has at least one reactive electrophilic group. By "reactive" electrophilic group or "reactive" organic electrophile, it is meant that the electrophilic group is sufficiently electron deficient to be capable of reacting with the organozinc reagent of the present invention. Preferably, the reactive electrophilic group is selected from the group of carboxylic acid halides, aldehydes, $\alpha,\beta$-unsaturated carbonyl compounds (i.e., esters, ketones, nitriles, amides, and carbamates), and epoxides.

Specific illustrations of the novel utility of the highly reactive zinc species and the organozinc reagents of the present invention produced from the highly reactive zinc are described below in the Examples. In certain situations the organozinc reagents can also react with copper (I) salts to produce organozinc reagents containing copper atoms, herein referred to as organozinc cuprate reagents.

Generally, the coupling reactions between the organozinc reagent and the organic electrophile are typically conducted in the same medium used to produce the organozinc reagent. The reaction is conducted under conditions designed to favor the production of the desired coupled product. Those conditions generally include low temperature, use of appropriate electrophiles, addition of the electrophile to the organozinc reagent and stirring with appropriate reaction times. One or more of these conditions will be appropriate for use in particular instances. Choice of some or all of them is within the ordinary artisan's skill.

Preferably, the reactions are carried out in an ethereal, polyethereal, or hydrocarbon solvent such as ethyl ether, tetrahydrofuran, methyl-t-butyl ether, glyme, diglyme, triglyme, benzene, and the like. If a hydrocarbon solvent is used, it preferably contains a secondary solubilizing agent such as N,N,N',N'-tetramethylethylenediamine, or the like. More preferably, the reactions are carried out in an ethereal or polyethereal solvent. Most preferably, highly solvating solvents, such as THF, methyl-t-butyl ether, glyme, diglyme, and triglyme, are used because they facilitate the oxidative addition reactions with the organic electrophiles.

Residual alkali metal salts, such as alkali metal cyanide, alkali metal halides, or combinations of alkali metal salts, are preferably present in the reaction mixture of the electrophiles and the organozinc reagents. Although not intended to be limited by any theory, it is believed that the excess alkali metal salt facilitates electron transfer to the organic compound.

The reagents and reactions of this invention are useful in the organic synthesis of organic compounds that are impossible to prepare by other techniques. In particular, the facility to react alkyl chlorides or vinyl and aryl bromides at low temperatures, the ability to modify chemical reactivity by formation of a zinc cuprate, and the ability to prepare various organozinc reagents which contain a wide range of functional groups, are all useful for designing organic synthetic procedures. As a result, these unique capabilities promote the use of the reagents and reactions of this invention in the organic synthesis of pharmaceutical compounds, insecticides, specialty chemicals, fine and rare organic chemicals, organic intermediates, herbicides, polymeric compounds, organic additives for polymer compositions, organic conductors, and organic information storage devices. Specific examples include the syntheses of two-dimensional, highly conducting polymers, prostaglandins, penicillins, tranquilizers, and carbocyclic anti-cancer agents. These syntheses are made more efficient, are economically feasible, and, in several cases, represent the only route possible. Thus, the present invention opens the synthetic and Investigatory arenas to the development and use of rare or previously unavailable organic compounds.

Preparation and Reactions of Organozinc Cuprate Reagents With Acid Chlorides and Enones Addition of copper(I) salts to the organozinc reagents described above result in organozinc cuprate complexes of unique and different chemical reactivity. The organozinc cuprate complexes are aliphatic, aryl, heterocyclic, arylalkyl, or polymeric zinc cuprates. Preferably, they are composed of a mixture or combination of an aliphatic, aryl, heterocyclic, arylalkyl, or polymeric zinc cuprate and an alkali metal salt. In these preferred mixtures the alkali metal salts are from the copper(I) salt and/or the zinc reagent. Significantly, the organozinc can contain a wide range of functional groups such as esters, nitriles, amides, ketones, carbamates, and other halides.

The copper(I) salts that are reactive with the organozinc reagents of the present invention are preferably copper(I) salts that are soluble in an ethereal, polyethereal, or hydrocarbon solvent. They include, but are not limited to, $CuCN \cdot 2LiBr$, $CuCN \cdot 2LiCl$, $CuCN \cdot 2LiI$, $CuCN \cdot LiBr$, $CuCN \cdot LiCl$, $CuCN \cdot LiI$, $CuI$, $CuBr$, $CuCl$, $CuF$, lithium thienylcyanocuprate, or other Cu(I) salts with nonprotic anions. More preferably, the Cu(I) salt is $CuCN \cdot 2LiBr$, $CuCN \cdot 2LiCl$, $CuCN \cdot 2LiI$, and lithium thienylcyanocuprate, or combinations thereof.

The reaction conditions used for the formation of the organozinc cuprate reagents are those typically designed to preserve the integrity of the organozinc cuprate reagents. These conditions include the exclusion of water and oxygen, temperature of less than about 200° C., preferably between about −140° C. and about 100° C., and more preferably between about −80° C. and about 30° C. The copper is usually added in an equimolar amount relative to the organozinc reagent, but can be added in an excess amount. The formation of the zinc cuprate reagents is typically carried out in the same medium used to produce the organozinc reagent.

Reaction of the organozinc reagents with acid halides, particularly acid chlorides, in the absence of a Cu(I) salt, typically afford complex mixtures of products. However, in the presence of a Cu(I) salt, such as $CuCN \cdot 2LiCl$, organozinc reagents can be converted into the corresponding copper derivatives, e.g., $RCu(CN)ZnX$ (R being the organo group), which can react with acid halides, preferably acid chlorides, to form dialkyl ketones, diaryl ketones, and mixed alkyl aryl ketones. Specific examples of these reactions are set forth in Example 3 and Table II.

These ketones can be produced from any of the organozinc reagents discussed above. They are preferably prepared starting with the zerovalent highly reactive zinc species prepared from zinc halides and cyanides. Preferably, they are prepared starting with the zerovalent highly reactive zinc species prepared from zinc cyanides because of the higher reactivity of the resultant zerovalent zinc species. If the ketones are produced starting with the zerovalent highly reactive zinc species prepared from zinc halides, Method C is preferably used for the preparation of the zerovalent zinc species because this route results in production of the ketones in greater than about 50%, and often greater than about 70%, reproducible yields.

Significantly and unexpectedly, organozinc cuprates containing vinyl groups, i.e., vinyl organozinc cuprates, can be made starting with the zerovalent highly reactive zinc of the present invention. These vinyl organozinc cuprates react with acid halides, preferably acid chlorides, to form vinyl ketones. Significantly, any organic compound with a vinyl group and a stable leaving group, such as a halide, will react with the zerovalent highly reactive zinc of the present invention and Cu(I) salts to produce vinyl organozinc cuprates. These include organic vinyl compounds containing a wide range of functional groups such as ketones, carbamates, nitriles, etc.

Furthermore, organic dihalides react with the highly reactive zinc of the present invention and Cu(I) salts to form organozinc cuprates. Using these organozinc cuprates, organic dihalides couple with acid halides to form organic diketones. These diketones and the vinyl ketones discussed above are preferably prepared starting with the zerovalent highly reactive zinc species prepared from zinc halides and cyanides. Preferably, they are prepared starting with the zerovalent highly reactive zinc species prepared from zinc cyanides because of the higher reactivity of the resultant zerovalent zinc species. If the diketones and vinyl ketones are produced starting with the zerovalent highly reactive zinc species prepared from zinc halides, Method C is preferably used for the preparation of the zerovalent zinc species because this route results in production of the diketones and vinyl ketones in greater than about 50%, and often greater than about 70%, reproducible yields.

The conditions for any of these ketone formation reactions involving acid halides include temperatures of less than about 200° C., preferably between about −140° C. and about 100° C., more preferably between about −80° C. and about 30° C., and the absence of oxygen or protic solvents. The organozinc cuprates and acid halides are combined in approximately equivalent ratios, i.e., 0.8–1.2 moles organozinc cuprate to 0.8–1.2 moles acid halide (or to 1.8–2.2 moles acid halide for the preparation of the diketones). The acid halides can be any of a variety of acid halides, i.e., $RC(O)X$ wherein the organic radical R is aliphatic, aryl, heterocyclic, arylalkyl, or polymeric. Preferably, the organic radical R in the acid halides is an alkyl, aryl, or arylalkyl group. More preferably, the acid halides are of the formula $RC(O)X$ wherein R is a $C_{1-100}$ alkyl, $C_{1-100}$ aryl, or $C_{7-100}$ arylalkyl. Most preferably, R is a $C_{1-100}$ alkyl or a $C_{6-100}$ aryl. Of the acid halides, the halide group that is the most preferred is chloride.

Organozinc cuprate reagents of the present invention also undergo conjugate 1,4-addition reactions with $\alpha,\beta$-unsaturated species to form functionalized ketones. Significantly, little if any 1,2-addition products are formed. See Example 4 and Table III for specific examples. The $\alpha,\beta$-unsaturated species that undergo the 1,4-addition reactions can be any of a variety of $\alpha,\beta$-unsaturated species. For example, they can be $\alpha,\beta$-unsaturated ketones, aldehydes, esters, and amides; $\alpha$-substituted $\alpha,\beta$-unsaturated ketones, aldehydes, esters, and amides; $\beta$-substituted $\alpha,\beta$-unsaturated ketones, aldehydes, esters, and amides; and $\alpha,\beta$-disubstituted $\alpha,\beta$-unsaturated ketones, aldehydes, esters, and amides. The $\alpha,\beta$-unsaturated species can be acyclic, cyclic, aryl, and even sterically hindered. Preferably, the $\alpha,\beta$-unsaturated species are ketones, including $\alpha$- and $\beta$-substituted $\alpha,\beta$-unsaturated ketones. Specific examples include 2-cyclohexenone, 4-hexen-3-one, methyl vinyl ketone, 2-cyclopentenone, 3-methyl-2-cyclohexenone, 2-methyl-2-cyclopentenone, and 3,5,5-trimethyl-3-vinylcyclohexanone.

If the $\alpha,\beta$-unsaturated species are sterically hindered, i.e., if any group in the molecule hinders attack of the $\beta$-position, it is preferred that the reaction mixture contains $BF_3$ etherate or chlorotrimethylsilane (TMSCl), and more preferred that the reaction mixture contains both $BF_3$ etherate and TMSCl. These reagents perform the function of activation of the $\alpha,\beta$-unsaturated system. Other useful reagents such as this include alkyl phosphines.

Typically, the product yields of the 1,4-addition reactions using the organozinc cuprate reagents are greater than about 40%, and preferably greater than about 70%. The reaction conditions for the 1,4-addition reactions include temperatures of less than about 100° C., preferably between about −140° C. and about 100° C., more preferably between about −80° C. and about 30° C., and the absence of oxygen. Organozinc cuprates can react with a variety of other organic complexes as discussed hereinbelow. They can be used, for example, in the preparation of 2,3-disubstituted 1,3-butadienes, substituted α,β-unsaturated ketones, esters amides, and sulfones and intramolecular cyclizations.

Reactions of Organozinc Cuprates With Allylic Halids

Since the allyl moiety is an integral feature of many natural products and biosynthetic intermediates, allylic compounds have been of considerable synthetic importance. Substitution reactions of allylic halides with organometallic reagents have provided an important route for the synthesis of these allylic compounds. Many factors affect the regiochemistry of these reactions, including the nature of the leaving group, the degree of substitution at the two ends of the allylic system, the solvent system, the nature of the nucleophile and the catalyst. In general, substitution of allylic substrates with or without complete allylic rearrangement has been an unpredictable process. While considerable research has been done on the coupling reactions of allylic halides with a variety of organometallic reagents, in only a few instances were the desired results obtained.

In contrast, the organozinc cuprates of the present invention undergo highly regioselective γ-alkylation of allylic halides at temperatures between about −140° C. and about 125° C., preferably between about −100° C. and 100° C., and more preferably between about −78° C. and about 25° C. Not only are the additions highly regioselective, but the organozinc reagents can also be highly functionalized. See Example 5 and Table IV for specific reactions.

The highly reactive zinc produced by any of methods described herein can be used in this synthetic procedure. Preferably, the highly reactive zinc is prepared from zinc cyanides and halides, and more preferably zinc cyanides. If zinc halides are used, the highly reactive zinc produced by Method C is preferred at least because product isolation and purification is easier, and the yields are more reproducible. Significantly, the highly regioselective γ-alkylation of allylic halides is effective of a wide variety of allylic halides, including highly functionalized allylic halides containing remote, i.e., about 2 or more carbons away, ester, amide, nitrile, ketone, carbamate, halide, or epoxide groups. The allylic halide is preferably a $C_{3-150}$ aliphatic halide, more preferably a $C_{3-150}$ aliphatic chloride or bromide. Specific examples include crotyl chloride, cinnamyl chloride, and cinnamyl bromide.

The $S_N2'$ reaction product is typically formed in greater than an equimolar amount, i.e., 50:50, relative to the $S_N2$ reaction product. Preferably, it is formed in greater than about an 80:20 molar ratio relative to the $S_N2$ reaction product, more preferably in greater than about a 90:10 molar ratio, and most preferably in greater than about a 95:5 molar ratio. The total yield of the reaction is typically greater than about 70%, and often greater than about 80%.

Preparation of Functionalized 2,3-Disubstituted 1,3-Butadienes

The organozinc reagents of the invention can also be used in regioselective reactions with alkynes to form functionalized butadienes. For example, functionalized 2,3-disubstituted-1,3-butadienes can be readily prepared by reacting functionalized organozinc compounds with 1,4-dichloro-2-butyne, 1,4-dibromo-2-butyne, 1,4-ditriflate-2-butyne, 1,4-dibrosylate-2-butyne, or 1,4-ditosyloxy-2-butyne mediated by Cu(I) salts.

It is known that Grignard reagents react with 1,4-dichloro-2-butyne to give a mixture of $S_N2$ and $S_N2'$ products. Several modifications, including the use of 1,4-dialkoxy-2-butyne, 1,4-ditosyloxy-2-butyne, 1,4-dimethylsulfinyloxy-2-butyne, or 1,4-bis[diethoxyphosphinyl-oxy]-2-butyne along with (RCuBr)MgBrLiBr, have been employed. However, these methods either require severe experimental conditions (90°–100° C., 40–45 hours) or limit the type of R groups. For 1,4-dialkoxy-2-butyne, the R group is limited to phenyl rings containing electron-withdrawing groups. For 1,4-ditosyloxy-2-butyne, only the unsubstituted phenyl ring was reported to be successful. For 1,4-dimethylsulfinyloxy-2-butyne and 1,4-bis[diethoxy-phosphinyloxy]-2-butyne, R was limited to alkyl groups. Use of Grignard reagents also precludes most functional groups.

The present invention provides organozinc compounds which are readily available by direct oxidative addition of organic compounds containing a stable leaving group, preferably organic halides, with highly reactive zinc. The highly reactive zinc can be prepared by any of the methods described herein. Preferably, the highly reactive zinc is prepared from zinc cyanides and halides, and more preferably zinc cyanides. If zinc halides are used, the highly reactive zinc produced by Method C is preferred at least because product isolation and purification is easier, and the yields are more reproducible. The organozinc reagents produced react with Cu(I) salts as described above to form organozinc cuprates. These organozinc cuprates react with alkynes to give highly regioselective $S_N2'$ products. For example, under similar conditions, organozinc cuprates react with 1,4-dichloro-2-butyne or 1,4-ditosyloxy-2-butyne to give exclusive $S_N2'$ attack yielding the corresponding 2,3-disubstituted-1,3-butadiene in good to excellent yields.

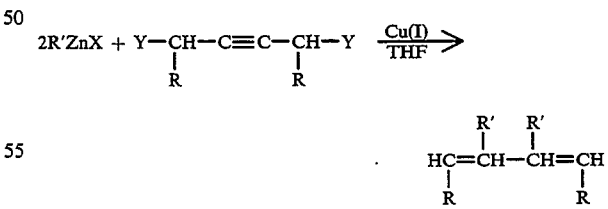

See Example 6 and Table V for specific embodiments of the foregoing reaction. The alkyne of the foregoing reaction can be any of a variety of molecules of the formula Y—CH(R)—C≡C—CH(R)—Y wherein R can be any alkyl, aryl, arylalkyl, or heterocyclic group, and Y can be a stable anionic leaving group, e.g., a halide, triflate, tosylate, brosylate, thiophenolate (—SC$_6$H$_5$), or phenolate (—OC$_6$H$_5$). Preferably, R is a $C_{1-100}$ alkyl, $C_{6-100}$ aryl, or $C_{7-100}$ arylalkyl, and Y is Cl, Br, triflate, tosylate, brosylate, thiophenolate, or phenolate. More preferably, R is a $C_{1-10}$ alkyl and phenyl, and Y is Cl, triflate, tosylate, and brosylate.

The preparation of functionalized 2,3-disubstituted 1,3-butadienes is typically carried out at temperatures of between about −100° C. and about 150° C., preferably between about −60° C. and about 70° C., and more preferably between about −20° C. and about 25° C. The functionalized 2,3-disubstituted 1,3-butadienes are typically formed by the methods of the present invention in greater than about 50% yields, and often in greater than about 70% yields.

Preparation of Functionalized Substituted α,β-Unsaturated Ketones, Esters, Amides, and Sulfones 2-Substituted-1-alkene compounds, vinyl halides, of the formula

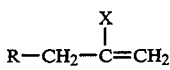

(wherein X=any of the stable anionic leaving groups listed for the organozinc reagents, preferably triflate or a halide, more preferably Br) are readily prepared by the cross-coupling of the organozinc reagents of the present invention with 2,3-disubstituted-propene compounds of the formula

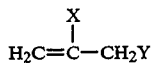

mediated with a Cu(I) salt, such as CuCN.2LiBr. The presence of the copper salt is advantageous for these coupling reactions because it increases yields and reaction rates. For example, in the presence of CuCN.2LiBr, the reactions are complete in about 15 minutes and the yields are excellent. It is believed that this is because of the formation of organozinc cuprates, as discussed above. The experimental results using various organozinc reagents are summarized in Table VI of Example 7. In each of the structures shown in this section, X and Y=any of the stable anionic leaving groups listed for the organozinc reagents in the discussion above, preferably triflate and a halide, and more preferably Br; and R=any aliphatic, aryl, heterocyclic, arylalkyl, or polymeric organic radical as in the organozinc reagents discussed above, preferably R is functionalized with any of the functional groups listed above for the organozinc reagents.

1-Alkene-2-zinc reagents, i.e., vinyl organozinc reagents, of the formula

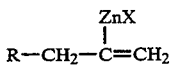

are readily prepared by oxidative addition of highly reactive zinc to the 2-substituted-1-alkenes. The conditions required for this oxidative addition reaction are as described above for the preparation of organozinc reagents. These 1-alkene-2-zinc reagents cross-couple with acid chlorides (RC(O)Cl), alkyl chloroformate (ClC(O)OR), carbamyl chlorides (R$_2$NC(O)Cl), and sulfonyl chlorides (ClS(O)OR), for example, using Pd(0) catalysts to produce α-substituted α,β-unsaturated ketones, α,β-unsaturated esters, α,β-unsaturated amides, and α,β-unsaturated sulfones, respectively, in high to excellent yields. The compounds of α,β-unsaturated ketones, esters, amides, and sulfones are extremely useful and versatile compounds. The experimental results using various vinyl organozinc reagents are summarized in Table VII of Example 8.

Traditionally, Aldol condensation reactions and the Friedel-Crafts reactions of acid chlorides, acids, and anhydrides with olefins have been the most important and effective methods for the preparation of α,β-unsaturated species. These methods are very limited for the syntheses of functionalized α-substituted α,β-unsaturated ketones, esters, amides, and sulfones. For example, most of the organozinc compounds, prepared by transmetallation from organolithium or Grignard reagents, couple with acid chlorides to give the corresponding carbonyl compounds; however, these methods preclude the presence of most functional groups.

With the present invention, highly reactive zinc, prepared by any of the reduction methods of a Zn(II) salt discussed herein, can be used in the preparation of highly functionalized α-substituted α,β-unsaturated ketones, esters, amides, and sulfones via the coupling reactions of highly functionalized vinyl organozinc reagents with acid halides, alkyl haloformates, carbamyl halides, and sulfonyl halides, preferably acid chlorides, alkyl chloroformates, carbamyl chlorides, and sulfonyl chlorides, using Pd(0) catalysts. The acid chlorides can be any acid chloride with functional groups that tolerate the conditions of their preparation. The Pd(0) catalyst can be Pd(PPh$_3$)$_4$, polymer-bound Pd(PPh$_3$)$_4$, Pd(dppe)$_2$ wherein dppe=1,2-bis(diphenylphosphino)ethane), or bis(dibenzylideneacetone) palladium. Preferably, the Pd(0) catalyst is Pd(PPh$_3$)$_4$. The reaction equations for a particular embodiment of this process are as follows:

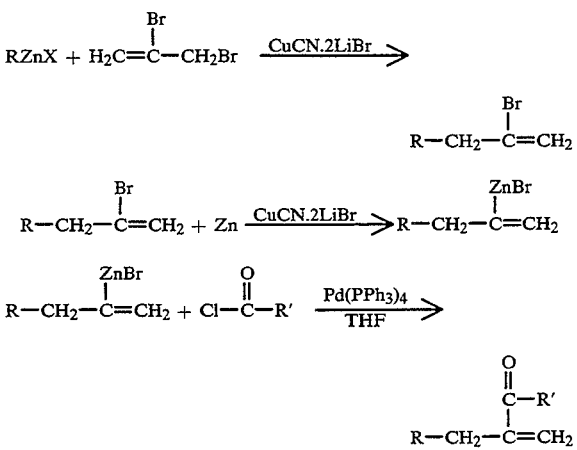

The preparation of substituted α,β-unsaturated ketones, esters, amides, and sulfones from the vinyl organozinc reagents is typically carried out with an effective amount of a Pd(O) catalyst at temperatures of between about −100° C. and about 100° C., preferably between about −50° C. and about 50° C., and more preferably between about −20° C. and about 30° C. By an "effective amount" of a Pd(O) catalyst, it is meant that there is a sufficient amount present to effect the reaction in a reasonable length of time, i.e., in less than five days. Typically, this is an amount of about 1–10 mole-%, and preferably about 1–5 mole-%, based on the amount of vinyl organozinc reagent present. The vinyl organozinc reagent and the reagent with which it couples to form the substituted α,β-unsubstituted species are present in an equimolar ratio, i.e., about 1 mole to 1 mole. The substituted α,β-unsaturated species are typically formed by the methods of the present invention in greater than about 50% yields, and often in greater than about 70% yields.

This approach can also be used to prepare β-substituted α,β-unsaturated ketones, esters, amides, and sulfones of the following structures:

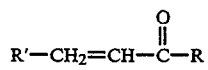

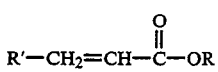

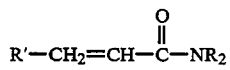

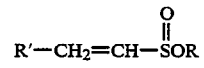

wherein R'=any aliphatic, aryl, heterocyclic, arylalkyl, or polymeric organic radical as in the organozinc reagents; preferably R' is functionalized with any of the functional groups listed herein for the organozinc reagents. R=any aliphatic, aryl, heterocyclic, arylalkyl, or polymeric organic radical.

Examples of reactions using this method of preparation are as follows:

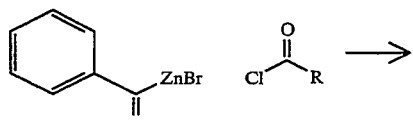

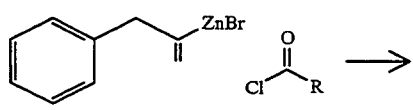

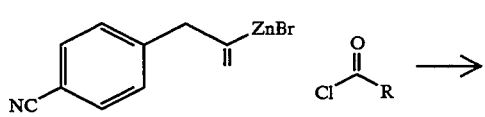

-continued

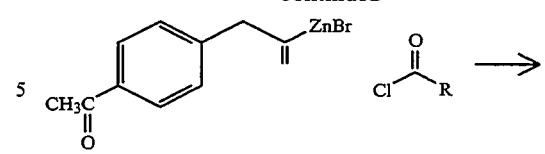

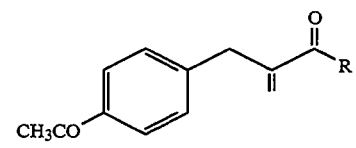

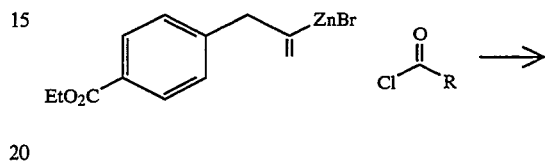

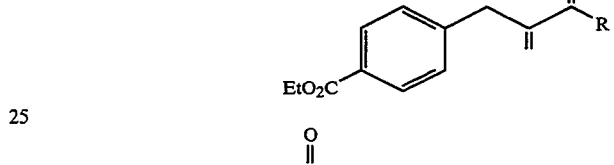

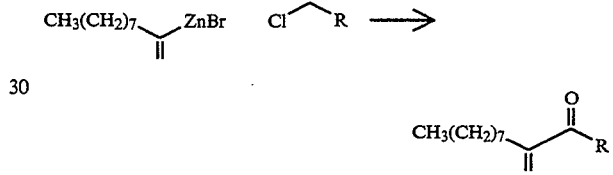

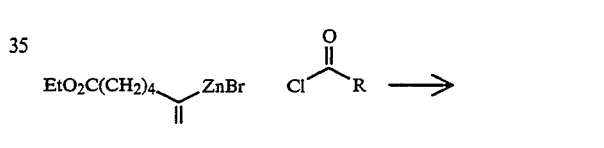

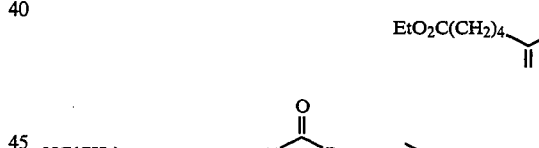

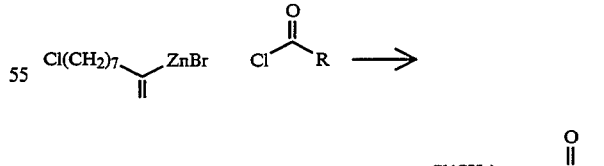

Reactions of Organozinc Reagent with Aryl or Vinyl Halides

Organozinc compounds can be readily cross-coupled with aryl, vinyl, and heterocyclic halides using a palladium catalyst. Known organozinc compounds prepared by a metathesis reaction from the corresponding organolithium reagent allow limited functionality to be tolerated. In contrast, the highly functionalized organozinc compounds of the present invention, prepared from highly reactive zinc, cross-couple readily with aryl and vinyl halides when catalyzed by a Pd(0) catalyst. This catalyst can be Pd(PPh3)4, polymer-bound Pd(PPh3)4, Pd(dppe)2 (wherein dppe=1,2-bis( diphenylphosphino)ethane), or bis(dibenzylideneacetone) palladium. Preferably, the Pd(0) catalyst is Pd(PPh3)4. The aryl and vinyl halides are preferably bromides and iodides. All functional groups are possible except for aldehydes.

These reactions are typically carried out with an effective amount of a Pd(O) catalyst at temperatures of between about −100° C. and about 100° C., preferably between about −50° C. and about 50° C., and more preferably between about −20° C. and about 30° C. By an "effective amount" of a Pd(O) catalyst, it is meant that there is a sufficient amount present to effect the reaction in a reasonable length of time, i.e., less than about 5 days. Typically, this is an amount of about 1–10 mole-%, and preferably about 1–5 mole-%, based on the amount of organozinc reagent present. The organozinc reagent and the reagent with which it couples are present in an equimolar ratio, i.e., about 1 mole to 1 mole. The reaction results in excellent yields producing highly functionalized symmetrical and unsymmetrical biaryls and symmetrical and unsymmetrical butadienes in greater than about 50% yields, and often in greater than about 70% yields. Example 9 and Table VIII presents some specific examples of these reactions.

Intramolecular Reactions Using Highly Reactive Zinc

The 1,4-conjugate addition chemistry to α,β-unsaturated ketones, aldehydes, esters, and amides represents an extremely important chemical transformation used in the synthesis of drugs, agrochemicals, monomers for polymers, and a wide range of specialty chemicals. This chemistry is primarily limited to intermolecular processes because the chemical transformations necessary to generate the nucleophile would destroy the α,β-unsaturated portion of the molecule. However, the present invention completely alters this picture because the highly reactive zinc of the invention will undergo a variety of reactions with highly functionalized organic compounds. For example, the highly reactive zinc undergoes oxidative addition to carbon-halogen bonds such as alkyl, aryl, and vinyl iodides, bromides, and chlorides in the presence of α,β-unsaturated ketones, aldehydes, esters, and amides. The resulting organozinc reagents can be transmetallated with a Cu(I) salt, e.g., CuCN.2LiX (X=I, Br, Cl, F), to yield an organozinc cuprate reagent which will undergo conjugate addition intramolecularly. Three generic examples are given below, wherein R=alkyl, aryl, vinyl, —OR, and —NR2. These reactions may also require the presence of activating agents such as BF3 etherate and/or TMSCl, as discussed above for α,β-unsaturated systems.

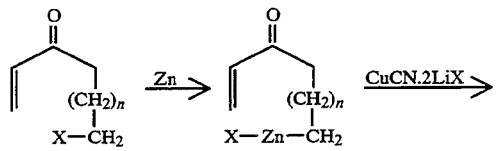

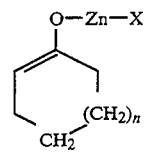

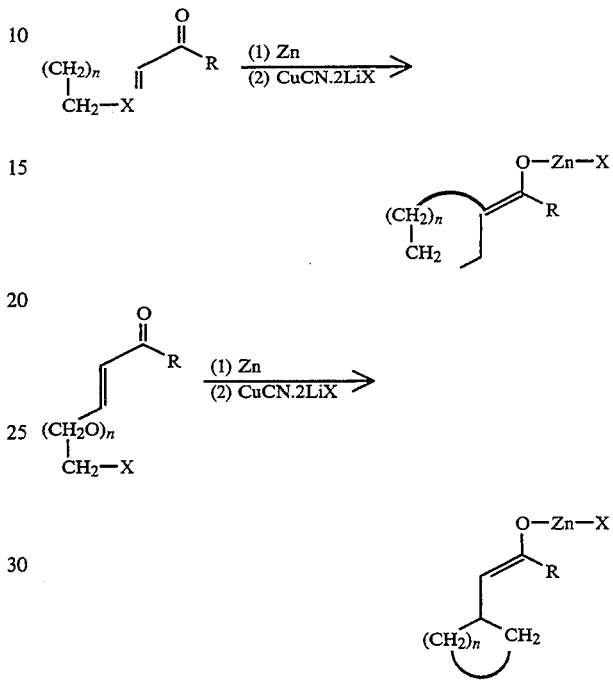

If the double bond is part of a ring system or if the alkyl chain containing the organic halide is part of a ring system, bicyclic and/or spiro ring systems will be possible. It should also be noted that other functional groups such as esters, ketones, nitriles, epoxides, amides, and carbamates may be present in the molecule and not be affected by these transformations. This chemistry is of particular value to the synthesis of drugs, agrochemicals and specialty chemicals. It represents a totally new class of chemical reactions.

Other typical reactions can be carried out intramolecularly with the zerovalent highly reactive zinc of the present invention. These include, the Reformatsky Reaction, Simmons-Smith Reaction, and the Blaise Reaction. A typical example of an intramolecular Reformatsky Reaction using a chloroacetate with the highly reactive zinc of the present invention and optional Cu(I) and/or Pd(0) catalysts, is as follows:

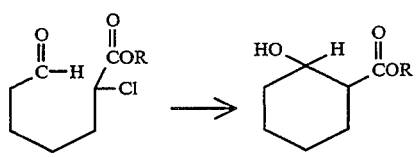

A typical example of an intramolecular Simmons-Smith Reaction with the highly reactive zinc of the present invention and optional Cu(I) and/or Pd(0) catalysts, is as follows:

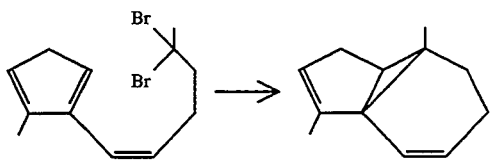

Examples of intramolecular Blaise Reactions with the highly reactive zinc of the present invention and optional Cu(I) and/or Pd(0) catalysts, are as follows:

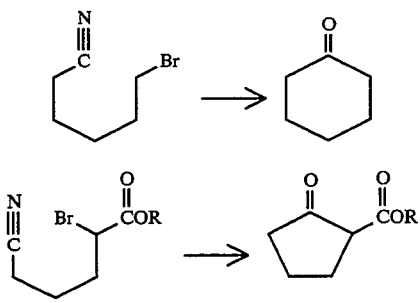

Thus the highly reactive zinc of the present invention, i.e., the zerovalent highly reactive zinc species prepared by contacting a Zn(II) salt with an alkali metal reducing agent to form a zerovalent highly reactive zinc species, can be used to form cyclic organic compounds. This method involves the steps of adding an organic compound with a reactive electrophilic group and a stable leaving group to the zerovalent highly reactive zinc species to produce an organozinc reagent containing a reactive electrophilic group, and coupling the carbon of the organozinc reagent to which the zinc is attached with the reactive electrophilic group to form an intramolecularly cyclized product. Although this coupling step may occur simply upon the addition of the highly reactive zinc species, a Cu(I) salt may be added as in the preparation of an organo-cuprate reagent and/or an effective amount of a catalyst may also be added to effect the cyclization. This catalyst may be any Pd(0) catalyst discussed herein for other reactions. The organic compound with the reactive electrophilic group and the stable leaving group includes any of the stable anionic leaving groups listed above in the discussion of the organozinc reagents, preferably it is a halide, and more preferably a chloride, bromide, or iodide. For certain intramolecularly cyclized reactions, the end of the molecule with a stable leaving group may include a second electrophilic group, such as an α-halo ester as in the intramolecular Reformatsky and Blaise reactions. Alternatively, the end of the molecule with a stable leaving group may include a carbon atom to which two stable leaving groups are attached, such as the dihalo-substituted carbon in the Simmons-Smith Reaction. The reactive electrophilic group of the organic compound can be any of the groups discussed herein that react with organozinc reagents to form a coupled product. Preferably, the reactive electrophilic group is an α,β-unsaturated species, a carbonyl group, a nitrile, and an olefin.

Preparation of Polymers from Highly Reactive Zinc

The ability to prepare highly functional organozinc reagents in quantitative yield provides an entry into a wide spectrum of novel polymers and polymeric materials. The preparation of polymers from functionalized monomers allows for the preparation of novel conducting polymers, water soluble polymers, and a wide spectrum of polymers with novel properties. For example, water soluble polymers have important biological uses, such as drug delivery systems, and industrial uses, such as in ion permeable membranes for the construction of organic batteries. These materials are also useful for the design of soluble catalysts which are of particular interest to industry to allow many transformations to be carried out in water rather than hydrocarbon solvents.

The polymers can be prepared from monozinc or dizinc aryl derivatives, such as

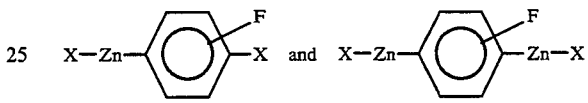

respectively, wherein X=any stable anionic leaving group listed in the discussion of organozinc reagents, preferably Cl, Br, I, triflate, tosylate, brosylate, —SC$_6$H$_5$, and —OC$_6$H$_5$. The functional group F can be H, CN, ester, amide, carbamate, epoxide, fluoride, chloride, sulfonic ester, sulfonamide, ketone, alkyl, aryl, vinyl, and a heterocyclic structure. The organic radical of the monozinc and dizinc derivatives include aryl groups, aliphatic groups, including alkyl or vinyl groups, arylalkyl groups, or heterocylic groups. Preferably, they are aryl, arylalkyl, and heterocyclic groups. Accordingly, a wide spectrum of functionalized alkyl, vinyl, and aryl polymers are possible from this chemistry.

The zerovalent highly reactive zinc species of the present invention can be used in the formation of polymers by combining the zerovalent highly reactive zinc species with an organic compound with at least two stable anionic leaving groups to form a dizinc derivative of an organozinc reagent, wherein the organic radical of the dizinc derivative of the organozinc reagent includes an aliphatic, heterocyclic, aryl, or arylalkyl group. A Cu(I) salt can be added to form a dizinc derivative of an organozinc cuprate reagent, in a manner analogous to that described in the discussion of the organozinc cuprate reagents. An organic electrophilic compound with at least two stable anionic leaving groups, such as an acid halide, is then added to the organozinc cuprate reagent to form a polymer.

Examples of new polymers and the reaction schemes by which they can be prepared from dizinc aryl derivatives are as follows:

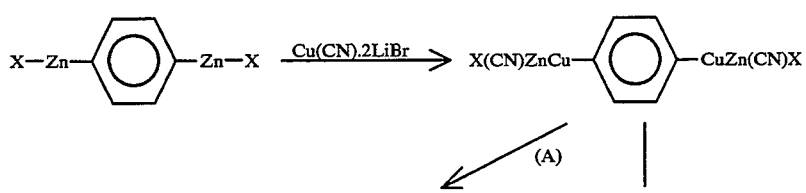

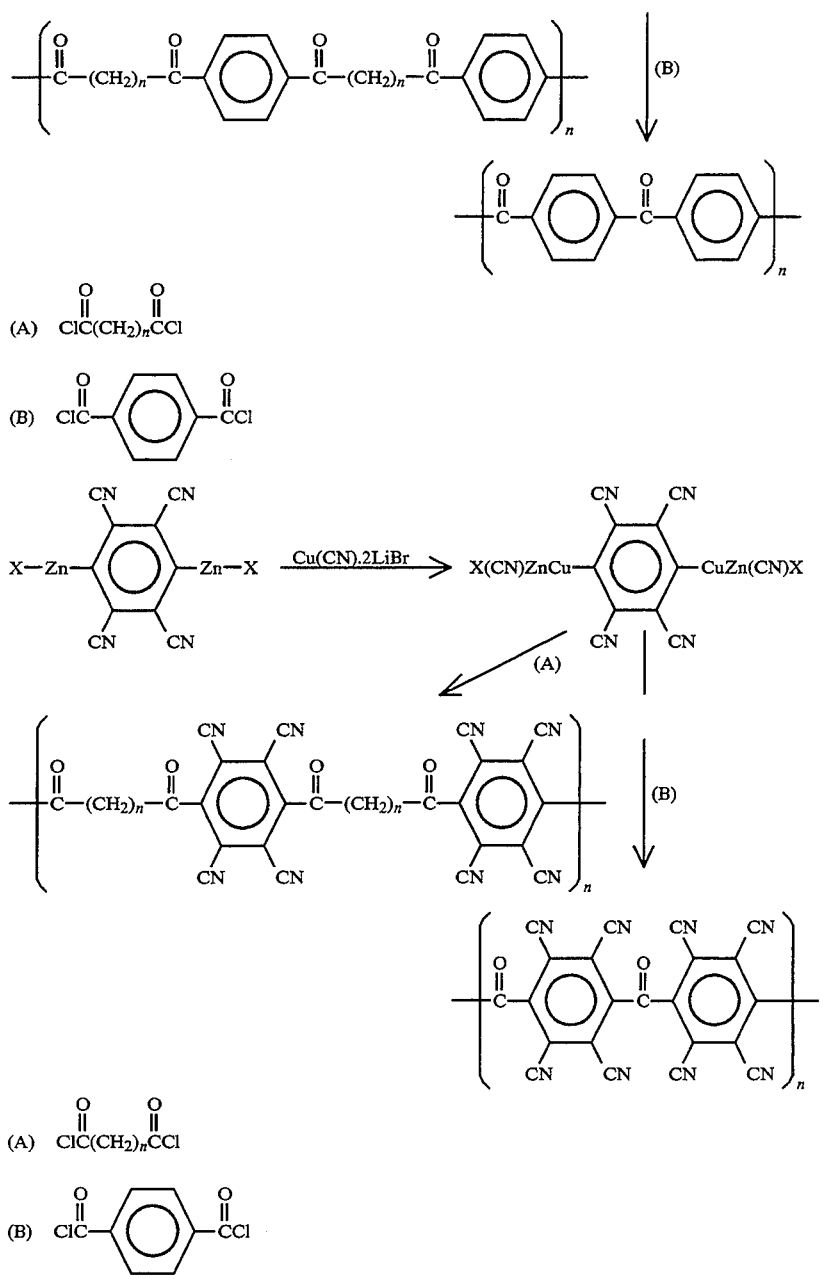

The monozinc aryl derivatives form polymers of the formula:

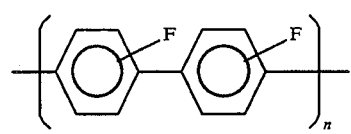

in the presence of an effective amount of a Pd(0) catalyst. By an "effective amount" of a Pd(O) catalyst, it is meant that there is a sufficient amount present to effect the reaction in less than about 5 days. Typically, this is an amount of about 1–10 mole-%, and preferably about 1–5 mole-%, based on the amount of organozinc reagent present. The Pd(0) catalyst can be Pd(PPh$_3$)$_4$, polymer-bound Pd(PPh$_3$)$_4$, Pd(dppe)$_2$ (wherein dppe = 1,2-bis(diphenylphosphino)ethane), or bis(dibenzylideneacetone) palladium. Preferably, the Pd(0) catalyst is Pd(PPh$_3$)$_4$. This approach also is effective in forming polymeric species with heterocyclic systems such as the following:

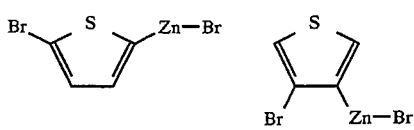

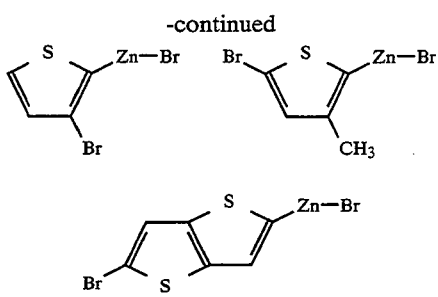

Polythiophene and polyphenylene have received extensive attention in recent years due to their nonlinear optical properties, electro-conductivity and many other valuable properties. There are many synthesis methods for polythiophene and polyphenylene. Three of the conventional methods are: 1) electro-polymerization; 2) dehydro-coupling polymerization of thiophene or benzene catalyzed by Lewis acids; and 3) dehalogenating polymerization of dihalothiophene or dihalobenzene using catalysts. Almost all methods are one pot reactions without exactly knowing the reaction intermediates. The electro-polymerization and dehydro-coupling polymerization give products containing mislinkage ($\alpha$-$\beta$ coupling) in the polymer chain. None of the products from these conventional methods are pure with respect to regiospecificity and stereospecificity, however. They are all insoluble and difficult to characterize.

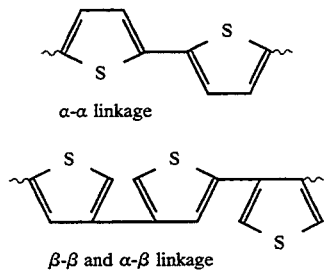

The conventional dehalogenating polymerization of 3-alkyldihalothiophene give products with highly regiospecific polymer chains, e.g., $\alpha$-$\alpha$ coupling; however, the polymer chain is still a random chain with respect to stereospecificity.

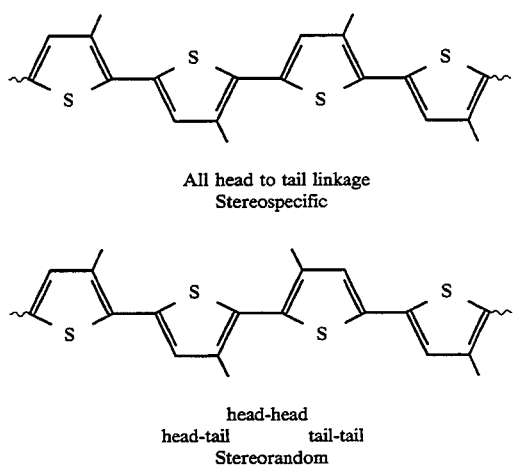

More and more research is concentrated on the chain specificity of polythiophene and polyphenylene because the chain structure has much to do with the electro-conductivity of the polymer. The zerovalent highly reactive zinc of the present invention can be used to form highly regiospecific, and often stereospecific polymers, such as the completely head to tail stereospecific poly-3-substituted-thiophene.

The highly reactive zinc of the present invention can be used in a quantitative regioselective manner for the preparation of dihalothiophene, dihalo-3-substituted-thiophene, and dihalobenzene, and in a facile polymerization method for highly regiospecific polythiophene, polyparaphenylene, and highly stereospecific poly-3-substituted-thiophene. The poly-3-substituted-thiophene can be substituted with a methyl or other alkyl group, a carboxylic acid group, nitrile group, or other functional group.

By combining the zerovalent highly reactive zinc species of the present invention, with an organic compound with at least two stable anionic leaving groups, a monozinc derivative of an organozinc reagent can be formed, wherein the organic radical includes an aliphatic, heterocyclic, aryl, or arylalkyl group. These organozinc intermediates undergo smooth polymerization in the presence of an effective amount of a Pd(0) catalyst. Preferably, this polymerization is conducted at temperatures of between about $-100°$ C. and $150°$ C., preferably between about $-20°$ C. and about $100°$ C. For example, 1.1 equivalent of highly reactive zinc reacts with 1.0 equivalent 2,5-dibromothiophene in THF under argon at room temperature to yield 100% regiospecific 2-bromo-5-bromozincthiophene. Also, 1.1 equivalent of the zinc reacts with 1.0 equivalent of 3-alkyl-2,5-dibromothiophene under the same reaction conditions to yield 100% regiospecific 3-alkyl-2-bromo-5-bromozincthiophene.

The yields of the polymers are greater than about 80% and often quantitative. For example, 100% poly-(2,5-thiophene) and poly-(3-alkyl,2,5-thiophene) with highly regiospecific, and even stereospecific, polymer chains can be formed by the method of the present invention. By "highly" regiospecific, and stereospecific, polymer chains it is meant that greater than about 80%, preferably greater than about 90%, and more preferably greater than about 98%, of the monomers are oriented in the polymer chains regiospecifically, and stereospecifically. Accordingly, these polymers are of a higher molecular weight with a more regular structure, and are more highly conducting, and have better nonlinear optical properties than any known to date.

This technology can also provide novel block polymers. Furthermore, this technology can be used to prepare highly regiospecific and stereospecific soluble polythiophenes and polyphenylenes, i.e., polymers with hydrophilic groups, such as a carboxylic acid ester.

The following Examples are intended to illustrate the above invention and should not be construed as to narrow its scope. One skilled in the art will readily recognize that these Examples suggest many other ways in which the present invention could be practiced. It should be understood that many variations and modifications may be made while remaining within the scope of the invention.

EXPERIMENTAL EXAMPLES

Melting points are uncorrected. $^1$H NMR (CDCl$_3$) spectra were recorded on a 200-MHz or a 360-MHz NMR spectrometer. $^{13}$C NMR spectra were recorded on a 50 MHz spectrometer. Analytical gas chromatography analysis was done using stainless steel columns or using a "megabore" glass capillary column. Stainless steel columns ($\frac{1}{8}$" diameter) were typically packed with Silicon OV-17 (3%) on Chromosorb ™ W-AW (100/120 mesh) with column lengths varying from 10 to 15 feet.

Reactions were carried out on a dual manifold vacuum/argon system. The Linde ™ prepurified grade argon was further purified by passing it through a 150° C. catalyst column (BASF R3-11) and then through a column of phosphorous pentoxide, followed by a column of granular potassium hydroxide. The handling of air-sensitive materials was performed, whenever possible, under argon in a Vacuum Atmospheres Company drybox. Chemical reagents were primarily purchased from commercial sources and were used as received. Anhydrous $ZnCl_2$, $ZnBr_2$, and $ZnI_2$ were purchased either from Cerac, Inc., Milwaukee, Wis., or Aldrich Chemical Co., Inc., Milwaukee, Wis. They were typically stored in the drybox and used as received. $Zn(CN)_2$ was purchased from Aldrich Chemical Co., Inc., Milwaukee, Wis. It was dried by heating at 250° C. under vacuum for 24 hours and stored in a drybox. THF and DME were freshly distilled before use from sodium/potassium alloy under a purified argon atmosphere.

Example 1

Preparation of Highly Reactive Zinc

Method A: One-Step Method From $Zncl_2$

A 50 mL, two-necked, round-bottomed flask was charged with lithium (0.35 g, 0.0504 mol), zinc chloride (3.27 g, 0.0240 mol), naphthalene (0.65 g, 0.00507 mol), and 1,2-dimethoxyethane (16.0 mL, 0.154 mol). The mixture was stirred at room temperature until the reduction was complete (about 15 hours), as evidenced by the disappearance of lithium and lack of formation of the bright green lithium naphthalenide anion. The activated zinc appeared as a fine black powder which settled out of solution after about one hour after cessation of stirring.

Method B: Two-Step Method From Preformed LiNp and $ZnCl_2$

Two 50-mL two-necked flasks, A and B, were equipped with rubber septa, condensers topped with argon inlets, and Teflon-coated magnetic stir bars. Flask A was charged with freshly cut lithium (0,213 g, 30.63 mmol) and a slight excess of naphthalene (3,987 g, 31.15 mmol). Flask B was charged with anhydrous $ZnCl_2$ (2.09 g, 15.57 mmol). Both of these operations were performed in an argon atmosphere drybox. The flasks were then transferred to a manifold system and fitted with argon inlets. Freshly distilled THF (15 mL) was added to both flask A and B via a syringe. The mixtures were stirred at room temperature. The solution in flask A changed from colorless to dark green almost immediately. The lithium was consumed in about two hours forming the preformed lithium naphthalenide (LiNp). The $ZnCl_2$/THF solution was then transferred dropwise to flask A via cannula over a period of 15 minutes.

Method C: Catalytic Method From $ZnCl_2$

Two 50-mL two-necked flasks A, and B, were equipped with rubber septa, condensers topped with argon inlets, and Teflon-coated magnetic stir bars. Flask A was charged with freshly cut lithium (0.2126 g, 30.63 mmol) and a catalytic amount of naphthalene (0.1994 g, 1,558 mmol). Flask B was charged with anhydrous $ZnCl_2$ (2.09 g, 15.57 mmol). Both of these operations were performed in an argon atmosphere drybox. The flasks were then transferred to a manifold system and fitted with argon inlets. Freshly distilled THF (15 mL) was added to both flask A and B via a syringe. The mixtures were stirred at room temperature. The solution in flask A changed from colorless to dark green almost immediately, followed by a change to reddish purple. The $ZnCl_2$/THF solution was transferred dropwise to flask A by a cannula at a rate that allowed the color of the solution to remain a dark green. The lithium was consumed in about 30 minutes and highly reactive zinc was found.

Method A: One-Step Method From $Zn(CN)_2$

A predried 50 mL, two-necked, round-bottomed flask was equipped with a rubber septum, a condenser topped with an argon inlet, and a Teflon-coated magnetic stir bar. It was then charged with freshly cut lithium (0,152 g, 21.90 mmol), $Zn(CN)_2$ (1.35 g, 11.49 mmol), naphthalene (0.144 g, 1.25 mmol). Freshly distilled THF (20 mL) was added. The mixture was stirred at room temperature until the green color disappeared, which evidenced that the reduction was complete (about 5 hours). The activated zinc appeared as a fine black powder. The formation of lithium naphthalenide by this method is faster than the rate of $Zn(CN)_2$ dissolution. Therefore, as little as 2-5 mole-% of naphthalene can be used as an electron carrier.

Method B: Two-Step Method From Preformed LiNp and $Zn(CN)_2$

Two 50-mL two-necked flasks A, and B, were equippic stir bars. Flask A was charged with freshly cut lithium (0.152 g, 21.9 mmol) and a slight excess of naphthalene (2.82 g, 22.0 mmol). Flask B was charged with anhydrous $Zn(CN)_2$ (1.35 g, 11.49 mmol). Both of these operations were performed in an argon atmosphere drybox. The flasks were then transferred to a manifold system and fitted with argon inlets. Freshly distilled THF (30 mL) was added to both flask A and B via a syringe. The mixtures were stirred at room temperature. The solution in flask A changed from colorless to dark green almost immediately. The lithium was consumed in about two hours forming the preformed lithium naphthalenide (LiNp). The preformed LiNp was then transferred dropwise to the $Zn(CN)_2$/THF dispersion via cannula over a period of 30 minutes.

Using any of the three methods for making zinc from any of the zinc salts, there are certain practical considerations that should be taken into account when choosing THF or DME as the solvent of choice. For instance, DME is preferred when higher reaction temperatures are desired. However, the formation of lithium naphthalenide is much more facile in THF than in DME. With respect to the procedure labelled "Method B" above, use of DME requires at least 2 hours longer for the lithium to be entirely consumed in the first step of preparing lithium naphthalenide than does THF. Furthermore, $ZnCl_2$ is more soluble in THF. This allows for more convenient transfer of the $ZnCl_2$ solution when necessary.

Using either Methods B or C above, the appearance of the highly reactive zinc formed depended on the amount of zinc halide used and on the speed of the addition. A slow addition, about three seconds per drop, resulted in an extremely fine black slurry of active zinc. This slurry took several hours to settle and was easily transferred by a cannula. With faster addition, about one second or less per drop, the active zinc formed was sponge shaped. The activities of the highly reactive zinc prepared from $ZnCl_2$, $ZnBr_2$, or $ZnI_2$ were similar.

The highly reactive zinc was typically used in the medium in which it was prepared. If desired, however, it can be washed several times with fresh solvent. This was typically done in situations in which naphthalene was perceived as presenting a problem with product isolation or if a different solvent was desired.

Example 2

Preparation of Organozinc Halides

Preparation Using Highly Reactive Zinc Prepared From $ZnCl_2$

Ethyl 4-iodobenzoate (1.934 g, 7.00 mmol) was added neat, via a syringe, to the highly reactive zinc, prepared as described in Example 1, Method C (15.40 mmol), at room temperature. The reaction mixture was stirred for 3 hours at room temperature. The solution was then allowed to stand for about 3 hours to allow the excess zinc to settle from the dark brown organozinc iodide solution. The preparation of organozinc compounds from various organic halides and the highly reactive zinc prepared as described in Example 1, Method C is summarized in Table IA below.

Preparation Using Highly Reactive Zinc Prepared From $Zn(CN)_2$

Preweighed p-bromotoluene (0.92 g, 5.38 mmol) was added neat via a syringe to the highly reactive zinc, prepared as described in Example 1, Method A or B (10.95 mmol). The reaction mixture was stirred at room temperature and monitored by GC. After 12 hours, the reaction was completed. The preparation of organozinc compounds from various organic halides and the highly reactive zinc prepared as described in Example 1, Method A is summarized in Table IB below.

TABLE IA

Preparation of Organozinc Compounds Using Highly Reactive Zinc Prepared From $ZnCl_2$ $$RX + Zn \xrightarrow[THF]{Temp, Time} RZnX$$

| No. | Organic Halides | Zn:RX (Ratio) | Temp (° C.) | Time (hours) | Yield[a] (%) |
|---|---|---|---|---|---|
| 1 | $Br(CH_2)_6Cl$ | 1.2:1 | 23 | 4 | 100 |
| 2 | $Br(CH_2)_7CH_3$ | 1.2:1 | 23 | 6 | 100 |
| 3 | $Br(CH_2)_3CO_2Et$ | 1:1 | 23 | 3 | 100 |
| 4 | p-$IC_6H_4Cl$ | 2:1 | 23 | 3 | 100 |
| 5 | p-$BrC_6H_4CN$ | 2:1 | Reflux | 3 | 90 |
| 6 | p-$BrC_6H_4CN$ | 3:1 | Reflux | 3 | 100 |
| 7 | p-$BrC_6H_4CO_2Et$ | 2:1 | Reflux | 2 | 100 |
| 8 | o-$BrC_6H_4CO_2Et$ | 2:1 | Reflux | 2 | 100 |
| 9 | m-$BrC_6H_4CO_2Et$ | 3:1 | Reflux | 4 | 100 |
| 10 | $Cl(CH_2)_3CO_2Et$ | 3:1 | Reflux | 4 | 100[b] |
| 11 | p-$BrC_6H_4CH_3$ | 2:1 | 23° C. | 12 | 31 |
| 12 | p-$BrC_6H_4CH_3$ | 2:1 | Reflux | 1 | 42 |

[a]The percent yield was determined by gas chromatography (GC) after hydrolysis with dilute HCl solution.
[b]In the presence of 2 equivalents of KI.

TABLE IB

Preparation of Organozinc Compounds Using Highly Reactive Zinc Prepared From $Zn(CN)_2$

| No. | Organic Halides | Zn:RX (Ratio) | Temp (°C.) | Time (hours) | Yield[a] (%) |
|---|---|---|---|---|---|
| 1 | p-$BrC_6H_4CH_3$ | 2:1 | 23° C. | 12 | 100 |
| 2 | p-$BrC_6H_4CH_3$ | 2:1 | 23° C. | 12 | 100[b] |
| 3 | p-$BrC_6H_4CH_3$ | 2:1 | Reflux | 1 | 100 |
| 4 | $Cl(CH_2)_3CN$ | 2:1 | Reflux | 1 | 100 |
| 5 | $Cl(CH_2)_3CO_2Et$ | 2:1 | Reflux | 1 | 100 |
| 6 | 5-$BrC_6H_4$-1,2,4-$(CH_3)_3$ | 2:1 | Reflux | 6 | 100 |

[a]The percent yield was determined by gas chromatography (GC) after hydrolysis with dilute HCl solution.
[b]Highly reactive zinc was prepared as described in Example 1, Method E. For all other examples, the highly reactive zinc was prepared as described in Example 1, Method D.

The highly reactive zinc was allowed to react with alkyl bromides (Entries 1–3 in Table IA) in a 1–1.2 to 1 molar ratio (Zn:RX) at room temperature for 3–6 hours to give the corresponding organozinc derivatives in 100% GC (gas chromatographic) yields. The formation of the organozinc species was monitored by GC and was based on the reduced product peak after hydrolysis with dilute HCl solution. The highly reactive zinc reacted with aryl iodides or bromides (Entries 4–5 in Table IA) in a 2:1 molar ratio at temperatures ranging from room temperature to refluxing THF temperatures in 2–3 hours to give the corresponding organozinc derivatives in 90–100% yield. By increasing the mole ratio of Zn:RX, 100% of RX can be converted to RZnX (Entry 6 in Table IA). The ortho, meta, and para functionalized aryl halides reacted with zinc to give the corresponding ortho, meta, and para substituted organozinc compounds (Entries 7–9 in Table IA and Entries 10–12 in Table II below). No scrambling of positions was observed.

There was no apparent direct oxidative addition of the highly reactive zinc of the present invention to alkyl or aryl chlorides using the zerovalent zinc prepared from zinc halides. However, in the presence of KI under refluxing conditions, alkylzinc species were formed from alkyl chlorides and the zerovalent zinc prepared from zinc halides (Entry 10 in Table IA). Although not intending to be limiting, this reaction presumably involves halogen exchange prior to organozinc formation. The use of zerovalent zinc prepared from zinc cyanide salts reacts with alkyl or aryl chlorides in the absence of initiators such as KI (compare Entry 10 in Table IA with Entries 4 and 5 in Table IB). As an example of the higher reactivity of the zerovalent zinc prepared from zinc cyanide salts, its oxidative addition to p-bromotoluene was compared to that of zerovalent zinc prepared from zinc halide salts (compare Entries 11 and 12 in Table IA with Entries 1–3 and 6 in Table IB).

Functionalized organozinc compounds can now be readily prepared from organic halides containing esters, nitriles, acetyls, ketones, carbamates, and other halides. The organozinc reagents are soluble in ethereal, polyethereal, and hydrocarbon solvents, light to dark brown in color, and stable under an argon or nitrogen atmosphere. The excess zinc can be easily separated from the organozinc species by allowing the zinc to settle out of solution for 1–3 hours and then transferring the clear organozinc solution via a cannula to another flask for further reaction.

Example 3

Table II summarizes the reactions of organozinc halides with various acid chlorides.

TABLE II

Reactions of Organozinc Halides Mediated by Copper with Acid Chlorides $$RX + Zn \longrightarrow [RZnX] \xrightarrow{CuCN \cdot 2LiBr} [RCu(CN)ZnX] \xrightarrow{R'COCl} RCOR'$$

| No. | RX | R'COCl | Zn:RX:R'COCl[a] | RCOR' | Yield[b] |
|---|---|---|---|---|---|
| 1 | Br(CH$_2$)$_7$CH$_3$ | PhCOCl | 1.5:1.0:0.9 | PhCO(CH$_2$O$_7$CH$_3$ | 92 |
| 2 | Br(CH$_2$)$_6$CN | PhCOCl | 1.1:1.0:0.8 | PhCO(CH$_2$)$_6$CN | 94 |
| 3 | Br(CH$_2$)$_6$Cl | PhCOCl | 1.0:1.0:1.0 | PhCO(CH$_2$)$_6$Cl | 85 |
| 4 | BrCH$_2$CH$_2$Ph | PhCOCl | 1.2:1.0:0.9 | PhCOCH$_2$CH$_2$Ph | 97 |
| 5 | Br(CH$_2$)$_3$CO$_2$Et | CH$_3$(CH$_2$)$_3$COCl | 1.0:1.0:0.9 | CH$_3$(CH$_2$)$_3$CO(CH$_2$)$_3$CO$_2$Et | 91 |
| 6 | Br(CH$_2$)$_3$CO$_2$Et | PhCOCl | 1.0:1.0:0.9 | PhCO(CH$_2$)$_3$CO$_2$Et | 95 |
| 6 | Cl(CH$_2$)$_3$CO$_2$Et | PhCOCl | 3.0:1.0:0.9 | PhCO(CH$_2$)$_3$CO$_2$Et | 91 |
| 7 | p-BrC$_4$H$_4$Me | CH$_3$(CH$_2$)$_3$COCl | 3.5:1.0:0.9 | CH$_3$(CH$_2$)$_3$COC$_6$H$_4$-p-Me | 86 |
| 8 | p-IC$_6$H$_4$CO$_2$Et | CH$_3$(CH$_2$)$_3$COCl | 2.0:1.0:1.0 | CH$_3$(CH$_2$)$_3$COC$_6$H$_4$-p-CO$_2$Et | 83 |
| 9 | p-IC$_6$H$_4$Cl | CH$_3$(CH$_2$)$_3$COCl | 1.5:1.0:1.0 | CH$_3$(CH$_2$)$_3$COC$_6$H$_4$-p-Cl | 90 |
| 10 | p-IC$_6$H$_4$CO$_2$Et | PhCOCl | 2.0:1.0:1.0 | PhCOC$_6$H$_4$-p-(CO$_2$Et) | 88 |
| 11 | m-BrC$_6$H$_4$CO$_2$Et | PhCOCl | 4.0:1.0:0.9 | PhCOC$_6$H$_m$-(COm-(CO2Et) | 83 |
| 12 | o-BrC$_6$H$_4$CO$_2$Et | PhCOCl | 2.0:1.0:0.9 | PhCOC$_6$H$_4$-o-CO$_2$Et | 92 |
| 13 | o-BrC$_6$H$_4$CO$_2$Et | CH$_3$(CH$_2$)$_3$COCl | 2.0:1.0:0.9 | CH$_3$(CH$_2$)$_3$COC$_6$H$_4$-o-CO$_2$Et | 94 |
| 14 | p-BrC$_6$H$_4$CN | CH$_3$(CH$_2$)$_3$COCl | 2.5:1.0:1.0 | CH$_3$(CH$_2$)$_3$COC$_6$H$_4$-o-CN | 71 |
| 15 | p-BrC$_6$H$_4$CN | PhCOCl | 3.0:1.0:0.9 | PhCOC$_6$H$_4$-p-CN | 73 |
| 16 | o-BrC$_6$H$_4$CN | PhCOCl | 3.0:1.0:0.9 | PhCOC$_6$H$_4$-o-CN | 98 |
| 17 | o-BrC$_6$H$_4$CN | CH$_3$(CH$_2$)$_3$COCl | 3.0:1.0:0.9 | CH$_3$(CH$_2$)$_3$COC$_6$H$_4$-o-CN | 97 |
| 18 | p-BrC$_6$H$_4$COCH$_3$ | CH$_3$(CH$_2$)$_3$COCl | 2.0:1.0:0.9 | CH$_3$(CH$_2$)$_3$COC$_6$H$_4$-p-(COCH$_3$) | 80 |
| 19 | PhCH=CHBr | CH$_3$(CH$_2$)$_3$COCl | 3.0:1.0:0.9 | CH$_3$(CH$_2$)$_3$C(O)CH=CHPh | 82 |
| 20 | PhCH$_2$Cl | PhCOCl | 1.5:1.3:0.9 | PhCOCH$_2$Ph | 81 |
| 21 | Br(CH$_2$)$_4$Br | PhCOCl | 3.0:1.0:2.0 | PhCO(CH$_2$)$_4$COPh | 78 |
| 22 | p-IC$_6$H$_4$I | CH$_3$COCl | 3.0:1.0:2.0 | CH$_3$COC$_6$H$_4$-p-(COCH$_3$) | 76 |

[a]Mole ratio
[b]Isolated yield (%).

The Copper-Mediated Coupling of Organozinc Halides with Acid Chlorides

The organozinc iodide solution of the reaction mixture from Example 2 (using zerovalent zinc from ZnCl$_2$) was transferred carefully via a cannula to another two-necked flask under an argon or nitrogen atmosphere leaving the excess zinc behind. This solution was cooled to −20° C. A solution prepared by mixing CuCN (0.651 g, 7.27 mmol) and anhydrous LiBr (1.273 g, 14.66 mmol) in THF (10 mL) was added to the organozinc iodide solution at −20° C. The reaction mixture was gradually warmed to 0° C. and stirred at 0° C. for about 15 minutes. The solution was then cooled to −25° C. Valeryl chloride (0.851 g, 7.02 mmol) was added neat to this solution via a syringe. The mixture was then poured into a saturated aqueous NH$_4$Cl solution (20 mL) and extracted with diethyl ether (3×20 mL). The combined organic layers were dried over anhydrous CaCl$_2$. The resultant crude product was chromatographed on flash silica gel using gradient elution (hexanes to remove naphthalene first, then hexanes/ethyl acetate) to give Ethyl 4-(1-oxo-pentyl)benzoate (Entry 8 in Table II, 1,360 g, 5,812 mmol) as a white crystalline solid in 83% isolated yield: mp 47.5-°48.0° C.; $^1$H NMR (360 MHz) δ 7.97-8.20 (m, 4H), 4.38 (q, J=7.1 Hz, 2H), 3.00 (t, J=7.3 Hz, 2H), 1.66-1.77 (m, 2H), 1.42 (t, J=7.1 Hz, 3H), 1.37-1.48 (m, 2H), 0.96 (t, J=7.2 Hz, 3H); $^{13}$C NMR δ 199.7, 165.6, 140.1, 133.9, 129.6, 127.7, 61.2, 38.5, 26.1, 22.3, 14.1, 13.8; IR (CCl$_4$) γ 3040, 2960, 1724, 1694, 1503 cm$^{-1}$. Anal. calcd. for C$_{14}$H$_{18}$O$_3$: C, 71.77; H, 7.74. Found C, 71.94; H, 7.80.

Organozinc iodides can be converted into the corresponding copper derivatives RCu(CN)ZnI by adding the soluble salt CuCN.2LiCl. This organometallic species reacts with various electrophiles to give the corresponding cross-coupled products in high yields. The present invention provides a very efficient way to prepare highly functionalized dialkyl ketones, diaryl ketones, mixed alkyl aryl ketones and vinyl ketones. In the cross-coupling reactions with acid chlorides, excess zinc is typically removed from the organozinc solution so it won't react with the acid chlorides, resulting in homocoupling of acid chlorides.

Using the method of the present invention, organozinc reagents couple with acid chlorides very rapidly to give the cross-coupled products in good to excellent yields. For example, o-cyanophenyl zinc bromide reacts with acid chlorides to give quantitative yields of coupling products (Entries 16 and 17 in Table II). The reaction of trans-styrene-β-zinc bromide with acid chloride to yield vinyl ketones provided an important route to synthesize vinyl ketones (Entry 19 in Table II). Diorganozinc bromides and iodides can also be prepared and react with acid chlorides to give diketones in good yield (Entries 21 and 22 in Table II). Significantly, this approach yields highly functionalized ketones not typically attainable by standard methods. Using the organozinc reagents in which the highly reactive zinc was prepared from Zn(CN)2 in a reaction with benzoyl chloride (0.69 g, 4.91 mmol), an 88% yield of 4-methylbenzoylphenone was obtained.

Other compounds prepared by the above method are: 1-phenyl-1-nonanone (Entry 1); 7-chloro-1-phenyl-1- heptanone (Entry 3); 1,3-diphenyl-1-propanone (Entry 4); ethyl 5-oxo-5-phenylpentanoate (Entry 6); 1-(p-methylphenyl)-1-pentanone (Entry 7); ethyl -o(1-oxopentyl)benzoate (Entry 8); 1-(p-chlorophenyl)- 1-pentanone (Entry 9); ethyl p-benzoylbenzoate (Entry 10); ethyl m-benzoylbenzoate (Entry 11); ethyl o-benzoylbenzoate (Entry 12); 1-(p-cyanophenyl)-1-pentanone (Entry 14); (p-cyanophenyl)phenylmethanone (Entry 15); 1-(o-cyanophenyl)phenylmethane (Entry 16); 1-(o-cyanophenyl)pentanone (Entry 17); 1-(p-acetylphenyl)-1-pentanone (Entry 18); 1,4-diacetylbenzene (Entry 22); as well as the following:

1-Oxo-1-phenyloctanenitrile: (Entry 2) mp 41.5°–42.0° C.; $^1$H NMR (360 MHz) δ 7.41–7.90 (m, 5H), 2.96 (t, J=7.2 Hz, 2H), 2.32 (t, J=7.1 Hz, 2H), 1.73 (m, 2H), 1.64 (m, 2H), 1.35–1.52 (m, 4H); $^{13}$C NMR δ199.8, 136.8, 132.7, 128.4, 127.7, 119.5, 38.0, 28.2, 28.1, 24.9, 23.6, 16.8; IR (CCl$_4$) γ 3061, 2938, 2245, 1690, 1598 cm$^{-1}$.

Ethyl 5-Oxononanoate: (Entry 5) $^1$H NMR (200 MHz) δ 4.13 (q, J=7.2 Hz, 2H), 2.48 (t, J=7.2 Hz, 2H), 2.25–2.55 (m, 6H), 1.85–1.93 (m, 2H), 1.51–1.59 (m, 2H), 1.25–1.40 (m, 2H), 1.26 (t, J=7.1 Hz, 3H), 0.90 (t, J=7.2 Hz, 3H); $^{13}$C NMR δ 210.3, 173.1, 60.2, 42.5, 41.4, 33.2, 25.8, 22.2, 18.8, 14.1, 13.7; IR (neat) γ 2958, 1736, 1714, 786 cm$^{-1}$.

Ethyl o-(1-oxopentyl)benzoate: (Entry 13) $^1$H NMR (200 MHz) δ7.30–7.95 (m, 4H), 4.34 (q, J=7.2 Hz, 2H), 2.81 (t, J=7.5 Hz, 2H), 1.64–1.75 (m, 2H), 1.31–1.52 (m, 2H), 1.35 (t, J=7.1 Hz, 3H), 0.93 (t, J=7.3 Hz, 3H); $^{13}$C NMR δ205.4, 166.5, 143.0, 131.7, 129.6, 129.4, 128.7, 126.0, 61.3, 42.3, 25.9, 22.1, 13.8, 13.6; IR (neat) γ 2958, 2960, 1718, 1597, 1277, 760 cm$^{-1}$. Anal. calcd. for C$_{14}$H$_{18}$O$_3$: C, 71.77; H, 7.74. Found: C, 71.62; H, 7.97.

trans-1-Phenylhept-1-en-3-one: (Entry 19) mp 32.0°–32.5° C.; $^1$H NMR (360 MHz) δ 7.35–7.59 (m, 6H), 6.75 (d, J=16.2 Hz, 1H), 2.66 (t, J=7.5 Hz, 2H), 1.60–1.68 (m, 2H), 1.35–1.45 (m, 2H), 0.94 (t, J=7.3 Hz, 3H); $^{13}$C NMR δ 200.6, 142.3, 134.6, 130.3, 128.9, 128.2, 126.3, 40.6, 26.5, 22.4, 13.9; IR (CCl$_4$) γ 3029, 2960, 1695, 1670, 1612, 1577, 1450 cm$^{-1}$.

1,2-Diphenylethanone: (Entry 20) mp 58°–59° C.; $^1$H NMR (200 MHz) δ7.20–8.15 (m, 10H), 4.27 (s, 2H); $^{13}$C NMR δ 197.5, 136.6, 134.5, 133.1, 129.4, 129.4, 128.6, 128.6, 126.8, 45.4; IR (CCl$_4$) γ 3066, 3030, 2958, 1685, 1600, 1274 cm$^{-1}$.

1,6-Diphenyl-1,6-hexanedione: (Entry 21) mp 103.5°–104.5° C.; $^1$H NMR δ 7.42–8.00 (m, 10H), 2.95–3.08 (m, 4H), 1.80–1.90 (m, 4H); $^{13}$C NMR δ 200.0, 136.9, 132.9, 128.5, 128.0, 38.4, 23.9; IR (CCl$_4$) γ 2937, 1691, 1598, 1581, 1448, 1459, 1267, 958 cm$^{-1}$.

Example 4

Copper-Mediated Conjugate Addition Reactions of Organozinc Halides to α,β-Unsaturated Ketones Ethyl 4-bromobutanoate (0.705 g, 3.62 mmol) was added neat, via syringe, to the highly reactive zinc (4.00 mmol), prepared according to the procedure outlined in Example 1, Method C from ZnCl$_2$, at room temperature. The reaction mixture was stirred at room temperature for 18 hours producing a dark solution of the alkylzinc bromide species. A solution prepared by mixing CuCN (0.327 g, 3.65 mmol) and anhydrous LiBr (0,636 g, 7.32 mmol) in THF (10 mL) was added at 0° C. The reaction mixture was stirred at 0° C. for 15 minutes, and then cooled to −78° C. Trimethylsilyl chloride (CH$_3$)$_3$SiCl (0.719 g, 6.62 mmol) and BF$_3$.Et$_2$O (0.800 g, 5.64 mmol) were added neat via a syringe, and the solution was stirred for 10–15 minutes. A solution of 2-cyclohexenone (0.269 g, 2.80 mmol) in THF (10 mL) was added dropwise over a period of 20 minutes to the reaction mixture at −78° C. The reaction mixture was stirred at −78° C. for 3 hours and slowly warmed to 0° C. After stirring at 0° C. for 1–2 hours, the reaction product was isolated and purified by a similar procedure to that described in Example 3 to give 3-(3-carbethoxypropyl)cyclohexanone (Entry 1 in Table III, 0,442 g) as an oil in 74% yield (92% GC yield): $^1$H NMR δ (200 MHz) 4.13 (q, J=7.2 Hz, 2H), 1.26–2.50 (m, 15H including 2.29 (t, J=7.2 Hz)), 1.26 (t, J=7.2 Hz, 2H); $^{13}$C NMR δ 211.1, 173.0, 60.0, 47.7, 41.2, 38.5, 35.6, 34.0, 30.8, 24.9, 21.8, 14.0; IR (neat) γ 2940, 1740, 1720, 1455, 1420, cm$^{-1}$; HREI calcd. for C$_{12}$H$_{20}$O$_3$ m/e 212.1413, found 212.1411.

Table III summarizes the reactions of organozinc halides with α,β-unsaturated ketones.

TABLE III

Copper-Mediated Conjugate Addition Reaction of Organozinc Halide with α,β-Unsaturated Ketones

| Entry | Organic Halide | Enone | Cu(I)$^a$ | Additives$^b$ | Products | Yield$^c$ |
|---|---|---|---|---|---|---|
| 1 | Br(CH$_2$)$_3$CO$_2$Et | cyclohexenone | A | BF$_3$.OEt$_2$ TMSCl | II (3-substituted cyclohexanone with (CH$_2$)$_3$CO$_2$Et) | 92 (74) |
| 2 | Br(CH$_2$)$_3$CO$_2$Et | I | A | TMSCl | II | 75 |
| 3 | Br(CH$_2$)$_3$CO$_2$Et | I | B | TMSCl | II<br>III (3-(thienyl)cyclohexanone) | 76 (55)<br>9 (8) |
| 4 | Br(CH$_2$)$_3$CO$_2$Et | I | B | BF$_3$.OEt$_2$ | III<br>II | 59 (39)<br>10 |

TABLE III-continued

Copper-Mediated Conjugate Addition Reaction of Organozinc Halide with α,β-Unsaturated Ketones

| Entry | Organic Halide | Enone | Cu(I)[a] | Additives[b] | Products | Yield[c] |
|---|---|---|---|---|---|---|
| 5 | Br(CH$_2$)$_6$Cl | (IV, pent-2-en-3-one) | A | BF$_3$·OEt$_2$ TMSCl | Cl(CH$_2$)$_5$CH$_2$-CH(-)-C(=O)-Et | 72 (77) |
| 6 | Br-cyclohexyl | (2-cyclohexenone) | I | A | BF$_3$·OEt$_2$ TMSCl | 3-cyclohexylcyclohexanone | 58 (66) |
| 7 | I-C$_6$H$_4$-CO$_2$Et | (2-cyclohexenone) | I | A | BF$_3$·OEt$_2$ TMSCl | 3-(4-carbethoxyphenyl)cyclohexanone | 68 |

[a] Reactions were performed in the prescence of 0.9 equivalents of the following copper salts: (A): CuCN·2LiBr in THF or (B): lithium 2-thienylcyanocyprate (0.25 M solution in THF) purchased from Aldrich Chemical Co.
[b] Added at −78° C. just prior to the addition of the enone.
[c] GC yields (%). Isolated yields are shown in parentheses.

Several variations were attempted using (3-carbethoxypropyl)zinc bromide as a target in order to optimize the 1,4-addition process. The best approach involved forming the zinc cuprate from the soluble CuCN/LiBr complex. A 92% yield (GC) of 1,4-adduct was obtained (Entry 1 in Table III). Another approach taken in an effort to optimize the conjugate addition process was the formation of a cuprate species ("R(2-th)Cu(CN)ZnX") from lithium 2-thienylcyanocuprate (LiCu(CN)2-th) in conjunction with the organozinc compounds.

Substituting lithium 2-thienylcyanocuprate for the CuCN/LiBr complex, and omitting boron trifluoride etherate from the reaction of the organozinc halide species with 2-cyclohexenone, gave a reasonable yield (76% GC) of the 1,4-adduct (Entry 3 in Table III). The reaction rate, temperature, and yield were similar to the reactions employing CuCN/LiBr. A noticeable amount (approximately 9% GC yield) of the product resulting from the 1,4-addition of the 2-thienyl group was also observed. This tendency was even more pronounced when the reaction was carried out in the presence of boron trifluoride etherate. In this reaction, 1,4-addition of the 2-thienyl group was the major product (59% GC yield) along with the usual 1,4-adduct (approximately 10% GC yield) (Entry 4 in Table III).

Other compounds prepared by the above method are listed below:

11-Chloro-5-methyl-3-undecanone: (Entry 5) $^1$H NMR (200 MHz) δ 3.53 (t, J=6.7 Hz, 2H), 2.14–2.48 (m, 4H including 2.40 (q, J=7.2 Hz, 3H)), 1.87–2.12 (m, 1H), 1.66–1.85 (m, 2H), 1.08–1.53 (m, 8H), 1.04 (t, J=7.3 Hz, 3H), 0.88 (d, J=6.6 Hz, 3H); $^{13}$C NMR δ221.5, 49.8, 45.0, 36.7, 36.4, 32.5, 29.2, 28.9, 26.8, 26.7, 19.8, 7.7; IR (neat) γ 2965, 2940, 2860, 1715, 1465, 1415, 720 cm$^{-1}$. HREI calcd. for C$_{12}$H$_{23}$$^{35}$ClO m/e 218.1437, found m/e 218.1432; calcd. for C$_{12}$H$_{23}$$^{37}$ClO m/e 220.1408, found m/e 220.1405.

3-Cyclohexylcyclohexanone: (Entry 6) $^1$H NMR (200 MHz) δ0.84–2.47 (m); $^{13}$C NMR δ212.7, 45.5, 44.6, 42.7, 41.6, 29.9, 29.8, 28.4, 26.5, 25.6; IR (neat) γ 2930, 2855, 1715, 1450, 1430 cm$^{-1}$. HREI calcd. for C$_{12}$H$_{20}$O m/e 180.1514, found m/e 180.1515.

3-(4-Carbethoxyphenyl)cyclohexanone: (Entry 7) $^1$H NMR (200 MHz) δ 7.96–8.07 (m, 2H), 7.24–7.37 (m, 2H), 4.37 (q, J=7.1 Hz, 2H), 2.97–3.18 (m, 1H), 2.28–2.68 (m, 4H), 1.66–2.26 (m, 4H) , 1.39 (t, J=7.2 Hz, 3H); $^{13}$C NMR δ210.01, 166.2, 149.2, 129.9, 128.9, 126.5, 60.8, 48.3, 44.5, 41.0, 32.3, 25.3, 14.2; IR (KBr) δ 3045, 2940, 1710 (br), 1610, 1445, 1420, 850 cm$^{-1}$. HREI calcd for C$_{15}$H$_{18}$O$_3$ m/e 246.1256, found 246.1255.

Example 5

Copper-Mediated Reactions of Organozic Halides with Allylic Halides

A solution prepared by mixing CuCN (0.495 g, 5.53 mmol, 1 equivalent) and anhydrous LiBr (0.965 g, 11.11 mmol, 2 equivalents) in THF (10 mL) under an argon atmosphere was precooled to −20° C. and added to (6-cyanohexyl)zinc bromide (5.46 mmol, 1 equivalent, in about 10 mL THF) at −20° C. The solution was then slowly warmed to 0° C. 1-Chloro-2-butene (0,544 g, 6.01 mmol, 1.1 equivalents) was added neat, via a syringe. The reaction mixture was stirred at this temperature for about 30 minutes. The reaction product was isolated and purified by a similar procedure to that described in Example 3 to give a 91% yield of a mixture containing the S$_N$2' and S$_N$2 products. The ratio determined by $^1$H NMR spectroscopy was S$_N$2':S$_N$2=97:3. 8-Methyldec-9-enenitrile (major product, Entry 2 in Table IV): $^1$H NMR (360 MHz) δ 5.62–5.72 (m, 1H), 4.87–4.97 (m, 2H), 2.33 (t, J=7.1 Hz, 2H), 2.07–2.12 (m, 1H), 1.60–1.71 (m, 2H), 1.23–1.35 (br s, 6H), 0.97 (d, J=6.7 Hz, 3H); $^{13}$C NMR δ 144.5, 119.6, 112.3, 37.6, 36.3, 28.7, 28.5, 26.7, 25.2, 20.1, 16.2; IR neat γ 3014, 2928, 2856, 2246, 966 cm$^{-1}$; Anal. calcd. for C$_{11}$H$_{19}$N: C, 79.94; H, 11.59; N, 8.47. Found C, 79.63; H, 11.81; N, 8.47.

Table IV summarizes the reactions of organozinc halides with various allylic halides.

TABLE IV

Reactions of RZnX With Allylic Halides Mediated by CuCN.2LiBr

| No. | RX | Allylic halide | Products[a] $S_N2':S_N2$ | Yield[b] |
|---|---|---|---|---|
| 1 | Br(CH$_2$)$_3$CO$_2$Et | H$_3$C—CH=CH—CH$_2$—Cl | 96:2 | 83 |
| 2 | Br(CH$_2$)$_6$CN | H$_3$C—CH=CH—CH$_2$—Cl | 97:3 | 91 |
| 3 | Br(CH$_2$)$_6$Cl | H$_3$C—CH=CH—CH$_2$—Cl | 98:2 | 94 |
| 4 | p-BrC$_6$H$_4$CO$_2$Et | H$_3$C—CH=CH—CH$_2$—Cl | 80:20 | 86 |
| 5 | Br(CH$_2$)$_3$CO$_2$Et | H$_3$C—CH$_2$Cl—CH=CH$_2$ | 100:0 | 87 |
| 6 | Br(CH$_2$)$_6$CN | H$_3$C—CH$_2$Cl—CH=CH$_2$ | 97:3 | 87 |
| 7 | p-IC$_6$H$_4$CO$_2$Et | H$_3$C—CH$_2$Cl—CH=CH$_2$ | 100:0 | 93 |
| 8 | Br(CH$_2$)$_3$CO$_2$Et | (C$_6$H$_5$)—CH=CH—CH$_2$—Cl | 97:3 | 86 |
| 9 | Br(CH$_2$)$_3$CN | (C$_6$H$_5$)—CH=CH—CH$_2$—Cl | 98:2 | 88 |
| 10 | Br(CH$_2$)$_2$Ph | (C$_6$H$_5$)—CH=CH—CH$_2$—Cl | 95:5 | 94 |
| 11 | Br(CH$_2$)$_3$CO$_2$Et | (CH$_3$)$_2$—CH=CH—CH$_2$—Br | 98:2 | 88 |
| 12 | Br(CH$_2$)$_6$CN | (CH$_3$)$_2$—CH=CH—CH$_2$—Br | 95:5 | 90 |
| 13 | Br(CH$_2$)$_2$Ph | (CH$_3$)$_2$—CH=CH—CH$_2$—Br | 95:5 | 89 |

[a]Ratio was determined from the crude product by $^1$H NMR.
[b]Isolated yield (%).

Both alkylzinc halides and arylzinc halides reacted with 3-chloro-1-butene to give 100% α-attack (S$_N$2') (Entries 5 and 7 in Table IV). Alkylzinc halides reacted with crotyl chloride and cinnamyl chloride to give about 97% of the S$_N$2' products (Entries 1–3 and 8–10). Even 1-bromo-3-methyl-2-butene, with the highly hindered γ-position, yields up to 95% of the S$_N$2' product (Entries 11, 12, and 14). The arylzinc halide reacts with crotyl chloride to give up to 80% of the S$_N$2' product. Temperature did not seem to affect the regioselectivity of attack of the alkyl or aryl zinc halides. Reactions run at −78° C. for about 10 minutes and then gradually warmed to room temperature had almost the same regioselectivity as the reaction run at 0° C. The following compounds were prepared by the above method: ethyl oct-6-enoate (Entry 5); ethyl 5,5-dimethylhept-6-enoate (Entry 11); and the following:

Ethyl 5-methylhept-6-enoate: (Entry 1) $^1$H NMR (360 MHz) δ 5.62–5.72 (m, 1H), 4.90–4.99 (m, 2H), 4.12 (q, J=7.1 Hz, 2H), 2.76 (t, J=7.5 Hz, 2H), 2.08–2.21 (m, 2H), 1.48–1.71 (m, 2H), 1.22–1.40 (m, 2H), 1.25 (t, J=7.1 Hz, 3H), 0.99 (d, J=6.7 Hz, 3H); $^{13}$C NMR δ 173.5, 144.1, 112.7, 60.0, 37.5, 35.7, 34.3, 22.6, 20.0, 14.1; IR (neat) γ 3077, 2960, 1739, 1640, 995, 912 cm$^{-1}$. HREI calcd. for C$_{10}$H$_{18}$O$_2$ m/e 170.1307, found 170.1301.

9-Chloro-3-methylnon-1-ene: (Entry 3) $^1$H NMR δ 5.60–5.73 (m, 1H), 4.88–4.97 (m, 2H), 3.53 (t, J=7.1 Hz, 2H), 2.06–2.13 (m, 1H), 1.72–1.80 (m, 2H), 1.38–1.45 (m, 2H), 1.25–1.31 (m, 6H), 0.98 (d, J=6.7 Hz, 3H); $^{13}$C NMR δ 144.8, 112.3, 45.1, 37.7, 36.5, 32.6, 29.0, 27.2, 26.9, 20.2; IR (neat) γ 3068, 3052, 2929, 1639, 910, 785 cm$^{-1}$; HREI calcd. for C$_{10}$H$_{19}$Cl m/e 174.1177, found 174.1178. Anal. calcd. for C$_{10}$H$_{19}$Cl: C68.75; H, 10.96. Found: C, 68.36; H, 10.67.

Ethyl 4-(1-Methyl-2-propenyl)benzoate: (Entry 4) $^1$H NMR δ (360 MHz) 7.21–8.02 (m, 4H), 5.90–6.02 (m, 1H), 5.01–5.11 (m, 2H), 4.36 (q, J=7.1 Hz, 2H), 3.43–3.58 (m, 1H), 1.38 (t, J=7.2 Hz, 6H); $^{13}$C NMR δ 166.5, 150.8, 142.3, 129.7, 129.0, 127.2, 113.8, 60.7, 43.1, 20.5, 14.3; IR (neat) γ 2978, 1726, 1610, 1587, 1415, 1392, 1367, 916, 584 cm$^{-1}$; HREI calcd. for C$_{13}$H$_{16}$O$_2$ m/e 204.1151, found 204.1146.

Undec-9-enenitrile: (Entry 6) $^1$H NMR (360 MHz) (cis and trans mixture) δ 5.35–5.45 (m, 2H), 2.33 (t, J=7.1 Hz, 2H), 1.93–2.14 (m, 2H), 1.6–1.7 (m, 5H), 1.3–1.5 (m, 2H), 1.2–1.45 (m, 6H); $^{13}$C NMR δ 131.2 (trans), 130.4 (cis), 124.6 (trans), 123.6 (cis), 120.0, 32.3, 29.3, 29.2, 28.7, 26.5, 25.2, 17.7, 16.9; IR (neat) γ 2927, 2856, 2247, 2463, 966 cm$^{-1}$; Anal. calcd. for C$_{11}$H$_{19}$N: C, 79.94; H, 11.59; N, 8.47. Found: C, 79.80; H, 11.46; N, 8.15.

Ethyl p-(2-butenyl)benzoate: (Entry 7, cis and trans mixture, trans is the major product) $^1$H NMR (200 MHz) δ 1.38 (t, J=7.1 Hz, 3H), 1.69 (d, J=4.75 Hz, 3H, trans) 1.69 (d, J=1.07 Hz, 3H, cis), 3.35 (d, J=4.61 Hz, 2H, trans), 3.45 (d, J=6.2 Hz, 2H, cis), 4.36 (q, J=7.13 Hz, 2H), 5.53–5.58 (m, 2H), 7.21–7.98 (m,4H); $^{13}$C NMR δ 166.6, 146.5, 146.4, 129.7, 129.6, 129.0, 128.4, 128.2, 128.2, 128.0, 127.1, 125.6, 77.64, 77.01, 76.37, 60.70, 39.0 (trans), 33.12 (cis), 17.8 (trans), 14.3, 12.8 (cis; IR (neat) γ 3023, 2856, 1716, 1610, 701, 761 cm$^{-1}$. Anal. calcd. for C$_{13}$H$_{16}$O$_2$: C, 76.44; H, 7.90. Found: C, 76.28; H, 7.81.

Ethyl 5-phenylhept-6-enoate: (Entry 8) $^1$H NMR (360 MHz) δ 7.15–7.30 (m, 5H), 5.88–6.08 (m, 1H), 4.06–4.14 (m, 2H), 4.10 (q, J=7.1 Hz, 2H), 3.21–3.27 (m, 1H), 2.28 (t, J=7.3 Hz, 1H), 1.45–1.80 (m, 4H), 1.23 (t, J=7.1 Hz, 3H); $^{13}$C NMR δ 173.4, 143.9, 141.8, 128.4, 127.5, 126.2, 114.2, 60.1, 49.6, 34.7, 34.1, 22.9, 14.2; IR (neat) γ 3081, 2979, 1735, 761, 701 cm$^{-1}$; HREI calcd. for C$_{15}$H$_{20}$O$_2$ m/e 232.1464, found 232.1461. Anal. calcd. for C$_{15}$H$_{20}$O$_2$: C, 77.55; H, 8.68. Found: C, 77.04; H, 8.68.

8-Phenyldec-9-enenitrile: (Entry 9) $^1$H NMR (360 MHz) δ7.12–7.32 (m, 5H), 5.80–6.00 (m, 1H), 5.0–5.04 (m, 2H), 3.22 (q, J=7.5 Hz, 1H), 2.27 (t, J=7.1 Hz, 2H), 1.63–1.73 (m, 2H), 1.55–1.62 (m, 2H), 1.18–1.25 (m, 6H); $^{13}$C NMR δ 144.3, 142.2, 128.3, 127.4, 126.1, 119.7, 113.9, 49.8, 35.2, 28.6, 28.4, 27.1, 25.2, 16.9; IR (neat) γ 3081, 3027, 2930, 2857, 2246, 1636, 1601, 1493, 1452 cm$^{-1}$. Anal. calcd. for C$_{16}$H$_{21}$N: C, 84.53; H, 9.31; N, 6.16. Found: C, 84.27; H, 9.49; N, 6.07.

3,5-Diphenyl-1-pentene: (Entry 10) $^1$H NMR (360 MHz) δ7.10–7.32 (m, 10H), 5.91–6.00 (m, 1H), 5.00–5.05

(m, 2H), 3.26 (m, 1H), 2.47–2.67 (m, 2H), 1.99–2.06 (m, 2H); $^{13}$C NMR δ 144.1, 142.2, 142.1, 128.5, 128.4, 128.3, 127.6, 126.2, 125.7, 114.3, 49.3, 37.0, 33.7.

8,8-Dimethyldec-9-enenitrile: (Entry 12) $^1$H NMR (360 MHz) δ 5.70–5.78 (m, 1H), 4.85–4.91 (m, 2H), 2.33 (t, J=7.1 Hz, 2H), 1.60–1.68 (m, 4H), 1.40–1.48 (m, 2H), 1.19–1.34 (m, 8H), 0.97 (s, 6H); $^{13}$C NMR δ 148.4, 124.6, 119.7, 110.1, 42.5, 29.4, 28.6, 26.6, 25.3, 24.2, 17.0; IR (neat) γ 2958, 2931, 2859, 2247, 1639, 1464, 1004, 910 cm$^{-1}$. Anal. calcd. for C$_{12}$H$_{21}$N: C, 80.38; H, 11.80; N, 7.81. Found: C, 80.02; H, 11.98; N, 7.71.

3,3-Dimethyl-5-phenylpent-1-ene: (Entry 13) $^1$H NMR (360 MHz) δ 7.13–7.28 (m, 5H), 5.78–5.87 (m, 1H), 4.94–4.99 (m, 2H), 2.48–2.54 (m, 2H), 1.05 (s, 6H); $^{13}$C NMR δ 148.1, 143.3, 128.3, 125.5, 110.7, 44.9, 36.7, 31.2, 26.7; IR (neat) γ 3086, 2960, 2929, 1641, 1604, 1496, 1454, 910 cm$^{-1}$.

Example 6

Preparation of Functionalized 2,3-Disubstituted-1,3-Butadienes

Use of highly functionalized organozinc compounds provides a new and effective route to functionalized 2,3-disubstituted-1,3-butadienes which are important intermediates in many organic syntheses. A typical procedure is as follows: a solution of CuCN.2LiBr (0.035 mol) in THF (15 mL) under argon was transferred to a precooled (−20° C.) solution of p-NCC$_6$H$_4$CH$_2$ZnBr (0.035 mol) in THF (30 mL). The solution was stirred for 15 minutes, then warmed to 0° C. 1,4-Dichloro-2-butyne (0.015 mol) was then added neat by syringe. The solution was stirred for 30 minutes at 0° C. and then at room temperature for 1 hour. The mixture was poured into a saturated NH$_4$Cl solution (20 mL) and extracted with diethyl ether (3×20 mL). The combined organic layers were dried over MgSO$_4$ and purified by column chromatography. 2,3-Di(p-cyanobenzyl)-1,3-butadiene (entry 8 in Table V) was obtained in 93% yield.

Table V summarizes the reaction of organozinc halides to produce various 2,3-disubstituted-1,3-butadienes.

TABLE V

Reactions of Organozinc Halides With Y—CH$_2$—C≡C—CH$_2$—Y

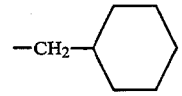

2RZnBr + Y—CH$_2$—C≡C—CH$_2$—Y $\xrightarrow{\text{CuCN.2LiBr}}_{\text{THF}}$ H$_2$C=C(R)—C(R)=CH$_2$ (Y = Cl or TsO)

| No. | Y | R | Yield$^a$ |
|---|---|---|---|
| 1 | Cl | —(CH$_2$)$_7$CH$_3$ | 95 |
| 2 | Cl | —(CH$_2$)$_6$Cl | 92 |
| 3 | Cl | —(CH$_2$)$_3$CO$_2$Et | 95 |
| 4 | Cl | —(CH$_2$)$_3$CN | 84 |
| 5 | Cl | —CH$_2$—C$_6$H$_{11}$ | 87 |
| 6 | Cl | —C$_6$H$_{11}$ | 82 |
| 7 | Cl | —CH$_2$C$_6$H$_5$ | 91 |
| 8 | Cl | —CH$_2$C$_6$H$_4$-p-CN | 93 |
| 9 | TsO | —(CH$_2$)$_7$CH$_3$ | (98) |
| 10 | TsO | —(CH$_2$)$_3$CO$_2$Et | (82) |
| 11 | TsO | —C$_6$H$_5$ | 88 |
| 12 | TsO | —CH$_2$C$_6$H$_5$ | (95) |
| 13 | TsO | —C$_6$H$_4$-p-COMe | 93 |
| 14 | TsO | —C$_6$H$_4$-p-CN | 97 |

$^a$Isolated Yield (%) GC yields are shown in parenthesis. All new compounds were identified by IR, NMR ($^1$H and $^{13}$C) and elemental analysis.

Example 7

Copper-Mediated Reactions of Organozinc Halides with 2,3-Dibromopropene

2-Bromo-1-alkene compounds (R—CH$_2$—C(Br)=CH$_2$) are readily prepared by the cross-coupling of organozinc reagents with 2,3-dibromopropene (H$_2$C=C(Br)—CH$_2$Br) mediated with CuCN.2LiBr. The presence of the copper salt improves the reaction rates and yields of these coupling reactions. In the presence of CuCN.2LiBr, the reactions are complete in about 15 minutes and the yields are excellent.

4-Bromobutylnitrile (1 equivalent, 35 mmol) was added neat directly to the highly reactive zinc prepared from ZnCl$_2$ according to Method C in Example 1 in THF (1.3 equivalents, 45 mmol) via syringe at room temperature. The mixture was stirred at reflux for ½ hour. Essentially all the 4-bromobutylnitrile was consumed, as indicated by gas chromatographic analysis. The excess zinc was allowed to settle out of the organozinc solution. After about 2–5 hours, the top dark brownish organozinc solution was slowly transferred via cannula to a CuCN.2LiBr/THF solution (3.5 mmol CuCN and 7.0 mmol LiBr in 20 mL THF) precooled to −30° C. After stirring for about 10 minutes, 2,3-dibromopropene (0.9 equivalents, 31.5 mmol) was added neat via syringe and stirred at this temperature for about 10 minutes, then at room temperature for another 30 minutes. After product isolation and purification, colorless liquid 2-bromohept-1-enenitrile (Entry 7 in Table VI) was recovered in 94% yield. $^1$H NMR 1.68–1.74 (m, 4H), 2.35–2.51 (m, 4H), 5.44 (d, J=1.7 Hz, 1H), 5.61 (t, J=0.9 Hz, 1H); $^{13}$C NMR 16.80, 23.92, 26.62, 40.22, 117.24, 119.25, 133.06; IR (neat) γ 2247, 1735, 1630 cm$^{-1}$.

Table VI summarizes this type of reaction.

TABLE VI

Preparation of 2-Bromo-1-Alkenes

RX + Zn $\xrightarrow{\text{Time}}_{\text{Temp.}}$ RZnX $\xrightarrow{\text{H}_2\text{C=C(Br)—CH}_2\text{—Br}}_{\text{CuCN.2LiBr}}$ R—CH$_2$—C(Br)=CH$_2$

| No. | RX | RX:Zn$^a$ | Temp (°C.) | Time (hours) | Yield$^b$ |
|---|---|---|---|---|---|
| 1 | PhI | 1:1.13 | 23 | 2 | 81 |
| 2 | p-BrC$_6$H$_4$CN | 1:2.5 | Reflux | 1 | 85 |
| 3 | p-BrC$_6$H$_4$COCH$_3$ | 1:2.0 | Reflux | 1 | 81 |

TABLE VI-continued

Preparation of 2-Bromo-1-Alkenes

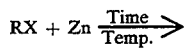

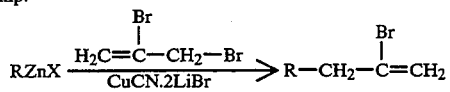

| No. | RX | RX:Zn[a] | Temp (°C.) | Time (hours) | Yield[b] |
|-----|-----|----------|------------|--------------|----------|
| 4 | p-IC$_6$H$_4$CO$_2$Et | 1:1.5 | Reflux | 0.3 | 90 |
| 5 | p-BrC$_6$H$_4$Cl | 1:1.7 | Reflux | 1.5 | 82 |
| 6 | Br(CH$_2$)$_3$CO$_2$Et | 1:1.2 | 23 | 2 | 96 |
| 7 | Br(CH$_2$)$_3$CN | 1:1.5 | Reflux | 0.5 | 94 |
| 8 | Br(CH$_2$)$_6$Cl | 1:1.2 | 23 | 2 | 88 |

[a]Molar ratio.
[b]Isolated yield (%). Compounds were fully characterized by $^1$H and $^{13}$C NMR, FT-IR, and Elemental analysis or HREI.

Example 8

Palladium-Mediated Preparation of Functionalized α-Substituted α,β-Unsaturated Ketones, Esters and Amides The preparation of 1-oxo-1-phenyl-2-methyleneheptanenitrile is representative of the preparations of α-substituted α,β-unsaturated ketones, esters, amides, and sulfones. 2-Bromohept-1-enenitrile (1 equivalent, 3.3 mmol) prepared as in Example 7 was added neat via syringe to highly reactive zinc prepared from ZnCl$_2$ according to Method C in Example 1 (1.5 equivalent, 5.0 mmol in about 20 mL THF) and stirred at reflux for 1 hour. Gas chromatography indicated that all the 2-bromohept-1-enenitrile was consumed. The excess zinc was allowed to settle. The top organozinc solution was transferred via cannula to another flask and benzoyl chloride (0.9 equivalents, 3.0 mmol) was added neat. The mixture was cooled to 0° C. and transferred via cannula to a precooled Pd(PPh$_3$)$_4$ (0.2 mmol in 10 mL THF). The solution was stirred at this temperature for 30 minutes. After the same isolation and purification procedure as described in Example 3, a 92% of 1-oxo-1-phenyl-2-methyleneheptanenitrile was recovered as a colorless liquid (Entry 7 in Table VII). $^1$NMR 1.65–1.72 (m, 4H), 2.34–2.54 (m, 4H), 5.65 (s, 1H), 5.88 (d, J=6.7 Hz, 1H), 7.40–7.75 (m, 5H); $^{13}$C NMR 16.73, 24.84, 27.12, 31.08, 119.40, 126.08, 128.05, 129.25, 132.10, 137.43, 146.92, 197.76; IR (neat) γ 2247, 1657 cm$^{-1}$. Anal. calcd for C$_{14}$H$_{15}$NO; C, 78.84; H, 7.10; N, 6.57. Found: C, 78.86; H, 7.06; N, 6.60.

The experimental results of Table VII demonstrate that vinyl organozinc reagents can be prepared by the oxidative addition of vinylbromides to the highly reactive zinc of the present invention. Using zerovalent zinc prepared from zinc halides, refluxing conditions are typically used to drive most of these reactions to completion. The coupling reactions of vinylzincbromides with acid chlorides, alkyl chloroformate, and carbamyl chlorides are listed in Table VII.

TABLE VII

Preparation of α-Substituted α,β-Unsaturated Ketones, Esters and Amides $$H_2C=C\begin{array}{c}R'\\|\\ZnBr\end{array} \xrightarrow{R''COCl}_{Pd(PPh_3)_4} H_2C=C\begin{array}{c}R'\\|\end{array}-\overset{O}{\overset{\|}{C}}-R''$$

| No. | R' | halides:Zn[a] | R'' | Yield[b] |
|-----|-----|---------------|-----|----------|
| 1 | —C$_6$H$_5$ | 1:1.2 | —C$_6$H$_5$ | 90 |
| 2 | p-CH$_2$C$_6$H$_4$CN | 1:2.5 | —C$_6$H$_5$ | 81 |
| 3 | p-CH$_2$C$_6$H$_4$Cl | 1:2.2 | —(CH$_2$)$_3$Me | 80 |
| 4 | p-CH$_2$C$_6$H$_4$CO$_2$Et | 1:2.0 | —C$_6$H$_5$ | 86 |
| 5 | p-CH$_2$C$_6$H$_4$CO$_2$Et | 1:2.0 | —(CH$_2$)$_3$Me | 88 |
| 6 | —C$_6$H$_5$ | 1:1.2 | —N(CH$_3$)$_2$ | 80 |
| 7 | —(CH$_2$)$_4$CN | 1:2.0 | —C$_6$H$_5$ | 92 |
| 8 | —(CH$_2$)$_7$Cl | 1:1.3 | —C$_6$H$_5$ | 82 |
| 9 | —(CH$_2$)$_4$CN | 1:2.0 | —OCH$_3$ | 78 |
| 10 | —(CH$_2$)$_4$CO$_2$Et | 1:1.2 | —OCH(CH$_3$)$_2$ | 81 |

[a]Molar ratio.
[b]Isolated yields (%). Compounds were fully characterized by $^1$H and $^{13}$C NMR, FT-IR, and elemental analysis or HREI.

Example 9

Palladium-Mediated Coupling Reactions of Organozinc Halides with Aryl and Vinyl Halides 4-Carbethoxyphenylzinc iodide (2.16 mmol, in about 10 mL THF) was transferred via a cannula to a THF solution of 5 mole-% Pd(PPh$_3$)$_4$ (0.127 g, 0.11 mmol) and 4-bromobenzonitrile (0.400 g, 2.19 mmol) at room temperature under an argon atmosphere. The solution was then stirred for 3 hours. The reaction product was isolated by a procedure similar to that described in Example 3. Ethyl 4-(4-cyanophenyl)benzoate (Entry 4 in Table VIII, 0,433 g, 1.73 mmol) in 80% yield was obtained as a crystalline solid: mp 114°–115° C.; $^1$H NMR (360 MHz) δ 7.60–8.21 (m, 8H), 4.42 (q, J =7.1 Hz, 2H), 1.42 (t, J=7.1 Hz, 3H); $^{13}$C NMR δ 165.9, 144.2, 143.1, 132.5, 130.4, 130.1, 127.7, 127.0, 118.5, 111.6, 61.0, 14.2; IR (CCl$_4$) γ 2981, 2231, 1722, 1608, 1276, 1109 cm$^{-1}$. HREI calcd. for C$_{16}$H$_{13}$NO$_2$ m/e 251.0947, found 251.0949. Anal. calcd. for C$_{16}$H$_{13}$NO$_2$: C, 76.48; H, 5.21; N, 5.57, Found: C, 76.25; H, 5.17; N, 5.31.

Table VIII summarizes the coupling reactions of various organozinc reagents with aryl and vinyl halides.

TABLE VIII

Coupling Reactions of RZnX with Aryl, Vinyl Halides Catalyzed by Pd(PPh$_3$)$_4$

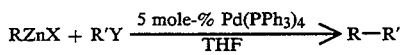

| No. | RZnX | R'Y | Product | Yield[a] |
|-----|------|-----|---------|----------|
| 1 | EtO$_2$C(CH$_2$)$_3$ZnBr | p-BrC$_6$H$_4$COCH$_3$ | 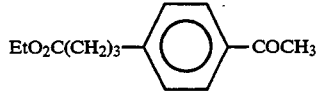 | 86 |

TABLE VIII-continued
Coupling Reactions of RZnX with Aryl, Vinyl Halides Catalyzed by Pd(PPh₃)₄

$$RZnX + R'Y \xrightarrow[\text{THF}]{\text{5 mole-\% Pd(PPh}_3)_4} R-R'$$

| No. | RZnX | R'Y | Product | Yield[a] |
|---|---|---|---|---|
| 2 | EtO₂C(CH₂)₃ZnBr | p-BrC₆H₄CN | EtO₂C(CH₂)₃—C₆H₄—CN | 93 |
| 3 | EtO₂C(CH₂)₃ZnBr | p-BrC₆H₄NO₂ | EtO₂C(CH₂)₃—C₆H₄—NO₂ | 90 |
| 4 | p-EtO₂C-C₆H₄-ZnI | p-BrC₆H₄CN | EtO₂C—C₆H₄—C₆H₄—CN | 80 |
| 5 | p-EtO₂C-C₆H₄-ZnI | p-IC₆H₄CO₂Et | EtO₂C—C₆H₄—C₆H₄—CO₂Et | 94 |
| 6 | m-EtO₂C-C₆H₄-ZnBr | p-BrC₆H₄CN | EtO₂C—C₆H₄—C₆H₄—CN (m,p) | 82 |
| 7 | p-NC-C₆H₄-ZnBr | p-BrC₆H₄CN | NC—C₆H₄—C₆H₄—CN | 95 |
| 8 | p-NC-C₆H₄-ZnBr | p-IC₆H₄CO₂Et | NC—C₆H₄—C₆H₄—CO₂Et | 82 |
| 9 | o-(CN)C₆H₄-ZnBr | m-BrC₆H₄CO₂Et | (o-CN)C₆H₄—C₆H₄(m-CO₂Et) | 93 |
| 10<br>11 | C₆H₅-C(=CH₂)-ZnBr | R''-C(=CH₂)-Br | C₆H₅-C(=CH₂)-C(R'')=CH₂ <br> R'' = H <br> R'' = CH₃ | 85(91)<br>86 |
| 12<br>13 | o-(CO₂Et)C₆H₄-CH=CH-ZnBr | R''-C(=CH₂)-Br | o-(CO₂Et)C₆H₄-CH=CH-C(R'')=CH₂ <br> R'' = H <br> R'' = CH₃ | 95<br>93 |

[a] Isolated yields (%). GC yields are shown in parentheses.

The highly functionalized organozinc compounds, prepared from the highly reactive zinc of the present invention, were found to cross-couple readily with aryl and vinyl halides when catalyzed by tetrakis(triphenylphosphine)palladium (Pd(PPh₃)₄). The reaction proceeded in excellent yields, producing highly functionalized symmetrical and unsymmetrical biaryls, and symmetrical and unsymmetrical butadienes (See Table VIII above). The following compounds were prepared by the above method: 4,4'-dicarbethoxybiphenyl (Entry 5); 4,4'-dicyanobiphenyl (Entry 7); 2-phenyl-1,3-butadiene (Entry 10); 2-methyl-3-phenyl-1,3-butadiene (Entry 11); and the following:

Ethyl 4-(4-acetylphenyl)butanoate: (Entry 1) $^1$H NMR (360 MHz) δ 7.30–7.91 (m, 4H), 4.13 (q, J=7.1 Hz, 2H), 2.71 (t, J=7.6 Hz, 2H), 2.58 (s, 3H), 2.32 (t, J=7.40 Hz, 3H), 1.91–2.02 (m, 2H), 1.25 (t, J=7.1 Hz, 3H); $^{13}$C NMR δ 197.6, 173.1, 147.2, 135.2, 128.6, 128.5, 60.3, 35.0, 33.5, 26.4, 26.1, 14.2; IR (neat) γ 2979, 2937, 1732, 1684, 1606, 845, 815 cm$^{-1}$. HREI calcd. for C$_{14}$Hphd 18O$_3$ m/e 234.1256, found 234.1257. Anal. calcd. for C$_{14}$H$_{18}$O$_3$: C, 71.77; H, 7.74. Found: C, 71.21; H, 7.62. Ethyl 4-(4-cyanophenyl)butanoate: (Entry 2) $^1$H NMR (360 MHz) δ 7.31–7.62 (m, 4H), 4.13 (q, J=7.1 Hz, 2H), 2.73 (t, J=7.7 Hz, 2H), 2.33 (t, J=7.3 Hz, 2H), 1.92–2.01 (m, 2H), 1.26 (t, J=7.2 Hz, 3H); $^{13}$C NMR δ 172.7, 146.9, 131.9, 129.0, 118.7, 109.6, 60.1, 34.8, 33.1, 25.7, 13.9; IR (neat) γ 2979, 2937, 2227, 1732, 1606, 844, 817 cm$^{-1}$. Anal. calcd. for C$_{13}$H$_{15}$O$_2$N: C, 71.86; H, 6.96; N, 6.45. Found: C, 71.25; H, 7.05; N, 6.30.

Ethyl 4-(4-nitrophenyl)butanoate: (Entry 3) $^1$NMR (360 MHz) δ 7.34–8.16 (m, 4H), 4.14 (q, J=7.2 Hz, 2H), 2.77 (t, J=7.7 Hz, 2H), 2.35 (t, J=7.3 Hz, 2H), 1.90–2.04 (m, 2H), 1.26 (t, J=7.1 Hz, 3H); $^{13}$C NMR δ 172.7, 149.2, 146.2, 129.1, 123.4, 60.1, 34.7, 33.1, 25.8, 14.0; IR (neat) γ 2981, 2938, 1732, 1604, 1598, 1520, 1346, 850, 746, 698 cm$^{-1}$. Anal. calcd. for C$_{12}$H$_{15}$NO$_4$: C, 60.75; H, 6.37; N, 5.90. Found: C, 60.63; H, 6.42; N, 5.70.

Ethyl 3-(4-cyanophenyl)benzoate: (Entry 6) mp 91.5°–92.0° C; $^1$H NMR δ 7.52–8.34 (m, 8H), 4.46 (q, J=7.2 Hz, 2H), 1.43 (t, J=7.1 Hz, 3H); $^{13}$C NMR δ 166.1, 144.5, 139.3, 132.6, 131.4, 131.3, 129.6, 129.1, 128.2, 127.7, 118.7, 111.4, 61.2, 14.3; IR (CCl$_4$) γ 3020, 2981, 2400, 2231, 1716, 1608, 1309, 1247, cm$^{-1}$. HREI calcd. for C$_{16}$H$_{13}$NO$_2$ m/e 251.0947, found 251.0949. Anal. calcd. for C$_{16}$H$_{13}$NO$_2$: C, 76.48; H, 5.21; N, 5.57. Found: C, 76.68; H, 5.36; N, 5.42.

Ethyl 3-(2-cyanophenyl)benzoate: (Entry 9) mp 81.5°–82.0° C.; $^1$H NMR (200 MHz) δ 7.40–8.25 (m, 8H), 4.41 (q, J=7.1 Hz, 2H), 1.41 (t, J=7.1 Hz, 3H); $^{13}$C NMR δ 166.0–144.4, 138.3, 133.7, 132.9, 132.9, 131.1, 130.0, 129.8, 129.7, 128.7, 127.9, 118.3, 111.3, 61.2, 14.3; IR (CCl$_4$) γ 3020, 2983, 2401, 2227, 1716, 1475, 1444, 1427, 1369, 1311, 1277, 1240, 930 cm$^{-1}$. Anal. calcd. for C$_{16}$H$_{13}$NO$_2$: C, 76.48; H, 5.21; N, 5.57. Found: C, 76.42; H, 5.18; N, 5.26.

Ethyl 2-(1,3-butadienyl)benzoate: (Entry 12) $^1$H NMR (200 MHz) δ 7.25–7.90 (m, 5H), 6.47–6.78 (m, 2H), 5.18–5.40 (m, 2H), 4.37 (q, J=7.1 Hz, 2H), 1.40 (t, J=7.1 Hz, 3H); $^{13}$C NMR δ 167.5, 138.6, 137.4, 132.2, 131.8, 131.2, 130.4, 129.0, 127.1, 126.7, 118.3, 61.0, 14.3; IR (neat) γ 2979, 1716, 1598, 1477, 1446, 1128, 1074, 1004, 754, 708 cm$^{-1}$. HREI calcd. for C$_{13}$H$_{14}$O$_2$ m/e 202.0994, found 202.0992.

Ethyl 2-(3-Methyl-1,3-butadienyl)benzoate: (Entry 13) $^1$H NMR (200 MHz) δ 7.26–7.92 (m, 4H), 6.77 (d, J=16.0 Hz, 1H), 5.10–5.13 (m, 2H), 4.38 (q, J=7.1 Hz, 2H), 2.01 (s, 3H), 1.41 (t, J=7.0 Hz, 3H); $^{13}$C NMR δ 167.6, 142.4, 139.0, 134.2, 131.9, 130.6, 128.9, 127.5, 126.9, 126.8, 117.8, 61.0, 18.7, 14.3; IR (neat) γ 3081, 1716, 1602, 1479, 1450, 1290, 1269, 1242, 964, 754, 710 cm$^{-1}$. HREI calcd. for C$_{14}$H$_{16}$O$_2$ m/e 216.1151, found 216.1150.

Example 10

Preparation of Polymers from Highly Reactive Zinc

Synthesis of Poly-(3-methyl,2,5-thiophene): 3-methyl,2,5-dibromothiophene (1.0263 g, 4.0095 mmol) in 10 mL dry, freshly distilled THF was transferred via cannula into a flask containing highly reactive zinc (4.6103 mmol, prepared according to Example 1, Method C, from ZnCl$_2$) which was in 20 mL dry THF under argon. The mixture was stirred for 2 hours at room temperature to yield 3-methyl-2-bromo-5-bromozincthiophene quantitatively. Pd(PPh$_3$)$_4$ (0.01 g, 0.008 mmol) in 5 mL dry THF was then transferred via cannula into the reaction mixture. A smooth polymerization happened even at room temperature and a red-brown precipitate appeared in 10 minutes. The mixture was further stirred for 2 hours at THF refluxing temperature (67° C.). The reaction mixture was then cooled to room temperature, and 10 mL 3M HCl solution was added. The mixture was stirred for 20 minutes. The mixture was poured into 50 mL MeOH, the deep-red precipitate was washed with several portions of MeOH and 3M HCl, and dried under vacuum for 24 hours at 80° C. The polymer yield was 0.3794 g (98.6%). The organozinc intermediate was verified by GC analysis using octane as the internal standard with the result of 100% regioselectivity and 100% yield.

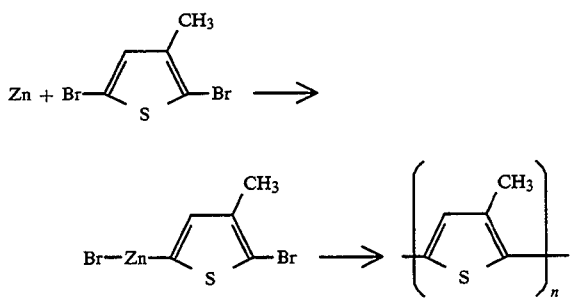

Synthesis of Poly-(2,5-thiophene): 2,5-dibromothiophene (0.9782 g, 4.0432 mmol) in 10 mL dry THF was transferred via cannula to highly reactive zinc (4.6391 mmol, prepared according to Example 1, Method C, from ZnCl$_2$) in 20 mL dry THF under argon. The reaction mixture was stirred for 2 hours at room temperature to yield 2-bromo-5-bromozincthiophene quantitatively. Then, Pd(PPh$_3$)$_4$ (0.01 g, 0,008 mmol) in 5 mL THF was transferred via cannula to the reaction mixture. The polymerization occurred at room temperature and was finished at refluxing THF temperatures for 2 hours. The reaction mixture was cooled, worked up with HCl as above, filtered, washed with MeOH and dilute acid, and dried under vacuum for 24 hours at 80° C. to yield Poly-(2,5-thiophene) 0.3298 g (100%).

Synthesis of poly-para-phenylene: 1,4-diiodobenzene (1.2977 g, 3.9332 mmol) in 10 mL dry THF was transferred via cannula to highly reactive zinc (4.1708 mmol, prepared according to Example 1, Method C, from ZnCl$_2$) in 20 mL dry THF under argon. The mixture was stirred for 3 hours at room temperature to yield 1-bromo-4-bromozincbenzene quantitatively (96%). Then, Pd(PPh$_3$)$_4$ (0.01 g, 0,008 mmol) in 5 mL dry THF was transferred via cannula to the reaction mixture. The polymerization occurred at room temperature. After refluxing for 2 hours at 67° C., the polymer (poly-paraphenylene) was isolated in the same manner as for the other polymers. The yield was 0.3175 g (100%). The polymer only lost 7% weight after extraction with hot chloroform over a period of 24 hours. Normally=20% is soluble in chloroform, which is indicative of the polymers of the present invention have a higher molecular weight and/or a more regular form of the structure.

The foregoing discussion and examples are illustrative of the invention. However, since many embodiments of the invention can be made without departing from the spirit and scope of the invention, the invention resides wholly in the claims hereinafter appended.

What is claimed is:

1. A zerovalent zinc species comprising a mixture of formally zerovalent zinc metal atoms and an alkali metal salt of cyanide.

2. A method for preparation of a zerovalent zinc species comprising contacting a $Zn(CN)_2$ species in a nonhydroxylic solvent with a reducing agent having a reduction potential of about −1.0 volt or more negative relative to a standard calomel electrode.

3. The method of claim 2 wherein the $Zn(CN)_2$ species comprises $Zn(CN)_2$ in coordination with an alkali metal halide salt.

4. The method of claim 2 wherein the reducing agent is an alkali metal reducing agent.

5. The method of claim 4 wherein the alkali metal reducing agent is an alkali metal salt of an electron transfer compound.

6. The method of claim 5 wherein the electron transfer compound is aromatic and has a reduction potential of about −0.5 volt or more negative relative to a standard calomel electrode.

7. The method of claim 6 wherein the reducing agent is an alkali metal salt of naphthalene, biphenyl, anthracene, or benzophenone.

8. A zerovalent zinc species prepared by the method of claim 2.

9. A zerovalent zinc species prepared by the method of claim 7.

10. The zerovalent zinc species of claim 1 further comprising an alkali metal salt of a halide.

11. The zerovalent zinc species of claim 1 wherein the alkali metal salt of cyanide is lithium cyanide.

12. The method of claim 4 wherein the alkali metal reducing agent is an alkali metal.

13. The method of claim 12 wherein the nonhydroxylic solvent has a boiling point that exceeds the melting point of the alkali metal.

14. (New) The method of claim 12 wherein the alkali metal is dissolved in a solvent selected from the group consisting of a glyme and an ether.

15. The method of claim 7 wherein the reducing agent is a complex of lithium and naphthalene.

16. A zerovalent zinc species comprising a mixture of formally zerovalent zinc metal atoms and an alkali metal salt, wherein the alkali metal salt includes an anion selected from the group consisting of cyanide, nitrate, nitrite, and combinations thereof.

17. The zerovalent zinc species of claim 16 further comprising an alkali metal salt of a halide.

18. The zerovalent zinc species of claim 16 wherein the anion of the alkali metal salt is selected from the group consisting of nitrate, nitrite, and combinations thereof.

19. A method for preparation of a zerovalent zinc species comprising contacting a Zn(II) salt in a nonhydroxylic solvent with a reducing agent having a reduction potential of about −1.0 volt or more negative relative to a standard calomel electrode, wherein the Zn(II) salt includes an anion selected from the group consisting of cyanide, nitrate, nitrite, and combinations thereof.

20. (Amended) The method of claim 19 wherein the anion of the Zn(II) salt is selected from the group consisting of nitrate, nitrite, and combinations thereof.

21. The method of claim 19 wherein the reducing agent is an alkali metal salt of an electron transfer compound.

22. The method of claim 19 wherein the reducing agent is an alkali metal.

23. A zerovalent zinc species prepared by the method of claim 19.

* * * * *

UNITED STATES PATENT AND TRADEMARK OFFICE
CERTIFICATE OF CORRECTION

PATENT NO. : 5,358,546

DATED : October 25, 1994

INVENTOR(S) : Reuben D. Rieke

Page 1 of 4

It is certified that error appears in the above-indentified patent and that said Letters Patent is hereby corrected as shown below:

On column 10, line 57, please insert --or-- after the word "arylalkyl"

On column 19, line 15, please insert --e.g.,-- after the word "compounds,"

On column 24, lines 10 and 11, please delete

"

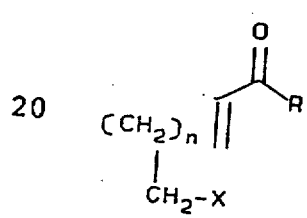

"

and substitute therefore--

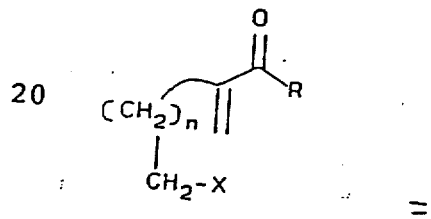

On column 24, line 25, please delete "(CH$_2$O)n" and substitute therefore -(CH$_2$)$_n$-

UNITED STATES PATENT AND TRADEMARK OFFICE
CERTIFICATE OF CORRECTION

PATENT NO.   : 5,358,546
DATED        : October 25, 1994
INVENTOR(S)  : Reuben D. Rieke It is certified that error appears in the above-indentified patent and that said Letters Patent is hereby corrected as shown below:

On column 31, line 49, please delete "(0,213 g," and substitute therefore --(0.213 g,--

On column 31, line 50, please delete "(3,987 g." and substitute therefore --(3.987 g,--

On column 32, line 3, please delete "1,558" and substitute therefore --1.558--

On column 32, line 23, please delete "(0,152 g." and substitute therefore --(0.152 g,--

On column 34, line 8, please delete "1" (under Time hours in 5th column) and substitute therefore --12--

UNITED STATES PATENT AND TRADEMARK OFFICE
CERTIFICATE OF CORRECTION

PATENT NO. : 5,358,546
DATED : October 25, 1994
INVENTOR(S) : Reuben D. Rieke

Page 3 of 4

It is certified that error appears in the above-indentified patent and that said Letters Patent is hereby corrected as shown below:

On column 35, line 60, please delete "1,360 g," and substitute therefore --1.360 g,--

On column 35, line 13, please delete "p-BrC$_4$H$_4$Me" and substitute therefore --p-BrC$_6$H$_4$ Me--

On column 36, line 17, please delete "PhCOC$_6$ H-m-(CO$_m$-(CO$_2$Et)" and substitute therefore --PhCOC$_6$H$_4$-m-(CO$_2$Et)--

On column 36, line 20, please delete "CH$_3$(CH$_2$)$_3$COC$_6$H$_4$-o-CN" and substitute therefore --CH$_3$(CH$_2$)$_3$COC$_6$H$_4$-p-CN--

On column 36, line 26, please delete "1.5:1.3:0.9" and substitute therefore --1.5:1.0:0.9--

On column 37, line 53, please insert --I-- under diagram.

On column 38, line 19, please delete "(0,636" and substitute therefore --(0.636--

On column 38, line 33, please delete "0,442" and substitute therefore --0.442--

On column 40, line 52, please delete "(0,544 g," and substitute therefore --(0.544 g,--

UNITED STATES PATENT AND TRADEMARK OFFICE
CERTIFICATE OF CORRECTION

PATENT NO. : 5,358,546
DATED : October 25, 1994
INVENTOR(S) : Reuben D. Rieke

It is certified that error appears in the above-indentified patent and that said Letters Patent is hereby corrected as shown below:

On column 42, line 9, please delete "96:2" and substitute therefore --96:4--

On column 41, line 17, please delete "$Br(CH_2)_3CN$" and substitute therefore --$Br(CH_2)_6CN$--

On column 45, line 44, please delete "$^1NMR$" and substitute therefore --$^1H$ NMR--

On column 46, line 41, please delete "0,433 g," and substitute therefore --0.433 g,--

On column 49, line 12, please delete "$C_{14}Hphd\ 180_3$" and substitute therefore --$C_{14}H_{18}O_3$--

Signed and Sealed this

Twenty-fifth Day of April, 1995

Attest:

BRUCE LEHMAN

*Attesting Officer*     *Commissioner of Patents and Trademarks*